(12) United States Patent
Wright

(10) Patent No.: US 11,116,525 B2
(45) Date of Patent: Sep. 14, 2021

(54) JOINT REVISION SURGERY APPARATUS

(71) Applicant: MAP Medical Solutions, LLC, Rupert, ID (US)

(72) Inventor: Mark B. Wright, Jackson, ID (US)

(73) Assignee: MAP Medical Solutions, LLC, Rupert, ID (US)

( * ) Notice: Subject to any disclaimer, the term of this patent is extended or adjusted under 35 U.S.C. 154(b) by 331 days.

(21) Appl. No.: 16/398,564

(22) Filed: Apr. 30, 2019

(65) Prior Publication Data

US 2019/0336143 A1    Nov. 7, 2019

Related U.S. Application Data

(60) Provisional application No. 62/665,894, filed on May 2, 2018.

(51) Int. Cl.
    *A61B 17/17*      (2006.01)
    *A61B 17/16*      (2006.01)

(52) U.S. Cl.
    CPC ........ *A61B 17/175* (2013.01); *A61B 17/1764* (2013.01); *A61B 17/1778* (2016.11); *A61B 17/1664* (2013.01); *A61B 17/1675* (2013.01); *A61B 17/1684* (2013.01)

(58) Field of Classification Search
CPC .............. A61B 17/175; A61B 17/1742; A61B 17/1764; A61B 17/1778; A61B 17/1675; A61B 17/1684; A61F 2/4607; A61F 2002/4619
See application file for complete search history.

(56) References Cited

U.S. PATENT DOCUMENTS

| | | | |
|---|---|---|---|
| 5,702,460 A | 12/1997 | Carls et al. | |
| 5,743,910 A * | 4/1998 | Bays | A61F 2/4607 606/99 |
| 5,885,296 A | 3/1999 | Masini | |
| 6,575,980 B1 * | 6/2003 | Robie | A61B 17/155 606/82 |
| 6,740,092 B2 | 5/2004 | Lombardo et al. | |
| 7,935,118 B2 * | 5/2011 | Vendrely | A61B 17/17 606/87 |
| 8,545,507 B2 * | 10/2013 | Vendrely | A61B 17/17 606/87 |
| 9,603,720 B2 * | 3/2017 | Kelley | A61B 17/155 |
| 9,668,749 B2 | 6/2017 | Gross | |
| 9,867,628 B2 * | 1/2018 | Macke | A61B 17/1742 |

* cited by examiner

*Primary Examiner* — Anu Ramana
(74) *Attorney, Agent, or Firm* — Richard D. Clarke

(57) ABSTRACT

The present application is directed a Joint Revision Surgery Apparatus which includes a blade guide block which has a plurality of blade guide slots and a central cavity. The blade guide block central cavity is positioned over the trunnion end of the existing prosthesis to be removed and secured to the prothesis. Straight, curved and compound curved knife blades are guided by the blade guide slots to cut the prothesis free. The securing of the guide blade block support apparatus against the femur is accomplished by the means of a male threaded T handle screw or male threaded eyebolt threading into one of the female threaded orifices in the blade guide block frame. The guide blocks in varying sizes and configurations, straight and curved knifes blades and related accessories may be sold as a complete kit. The Joint Revision Surgery Apparatus facilitates rapid, efficient and complete removal of an existing prosthesis during joint revision surgery.

20 Claims, 17 Drawing Sheets

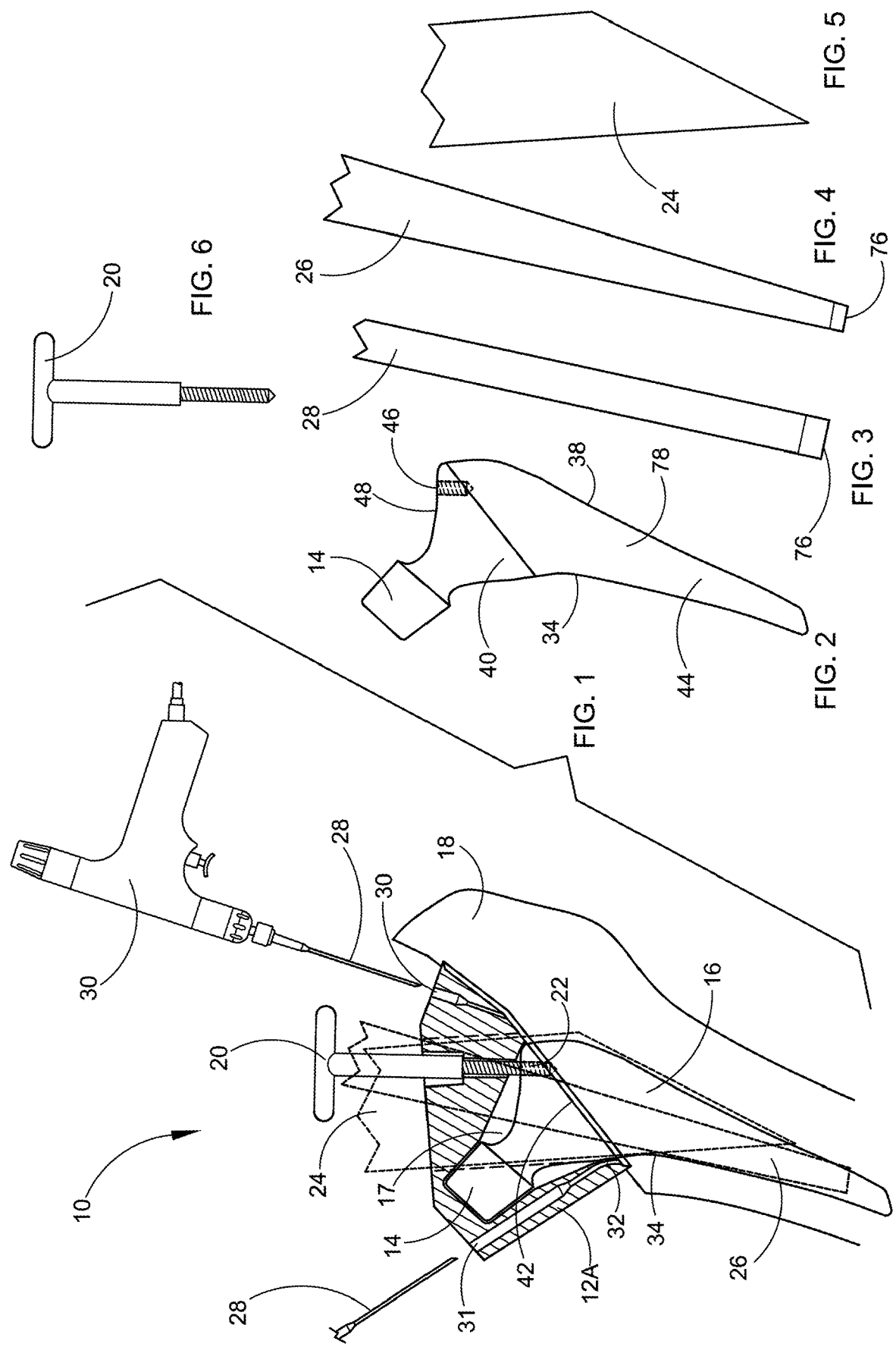

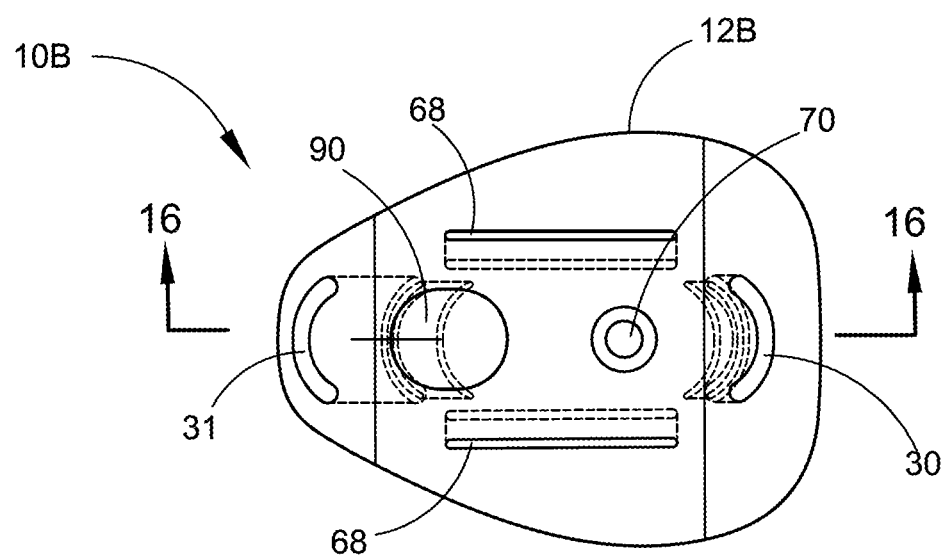
FIG. 15
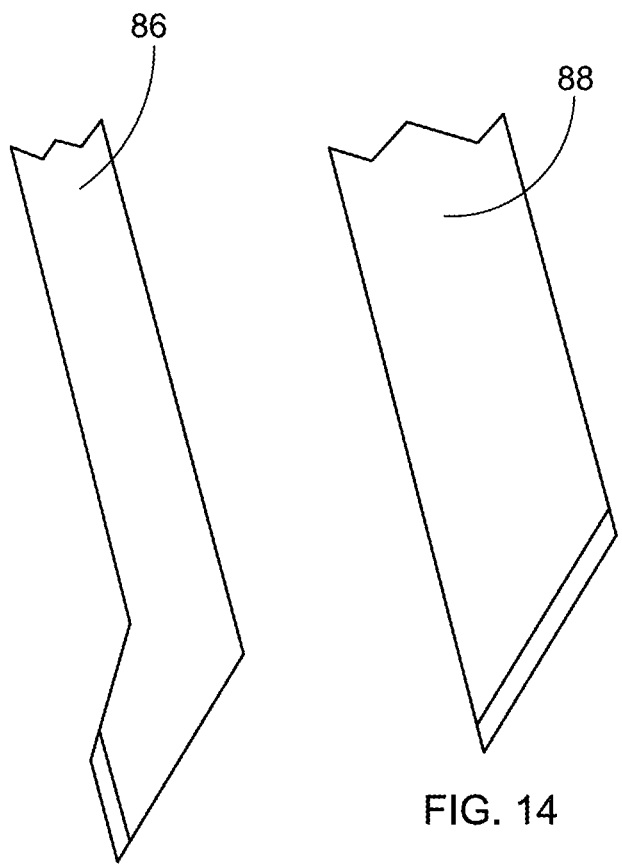
FIG. 14
FIG. 13

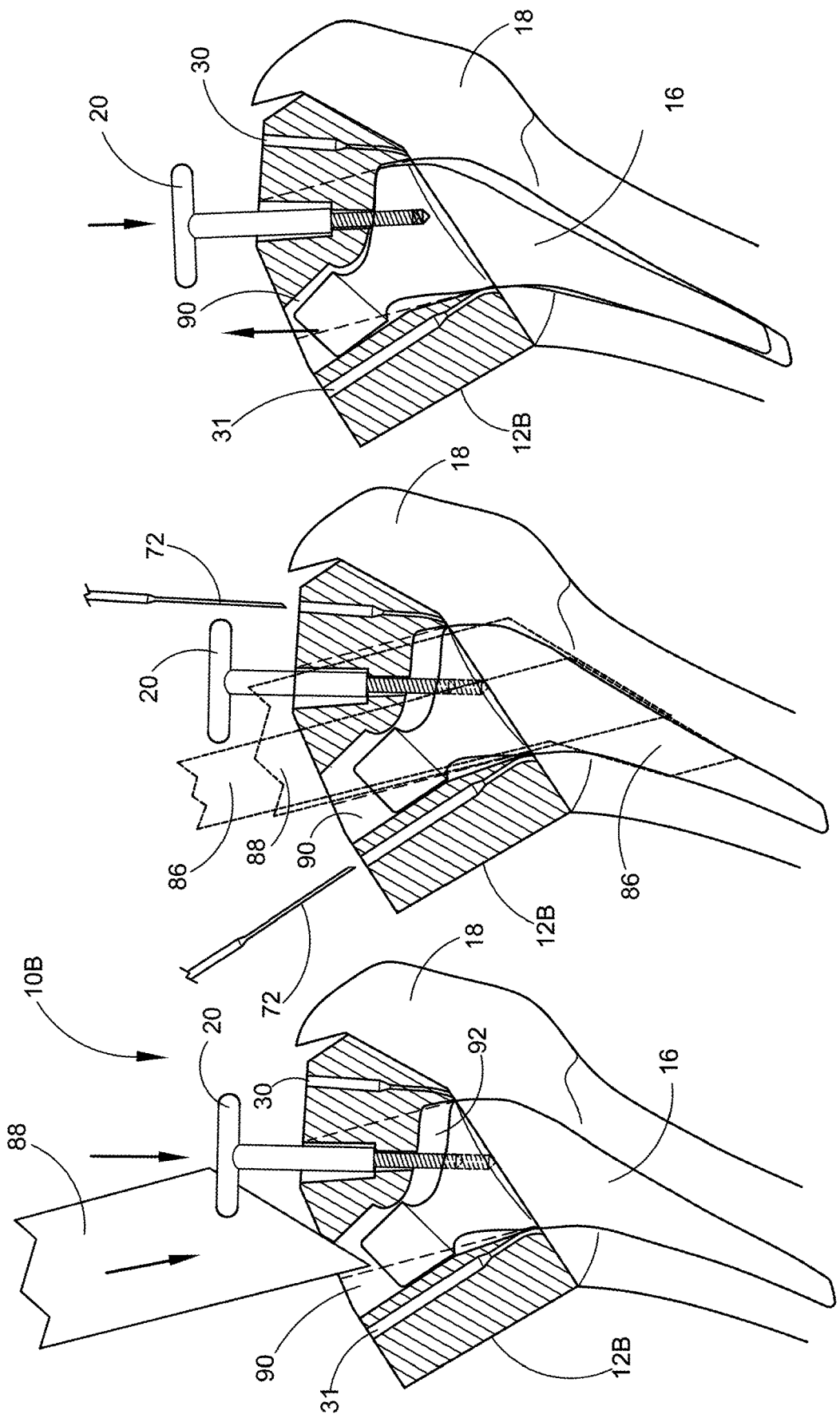

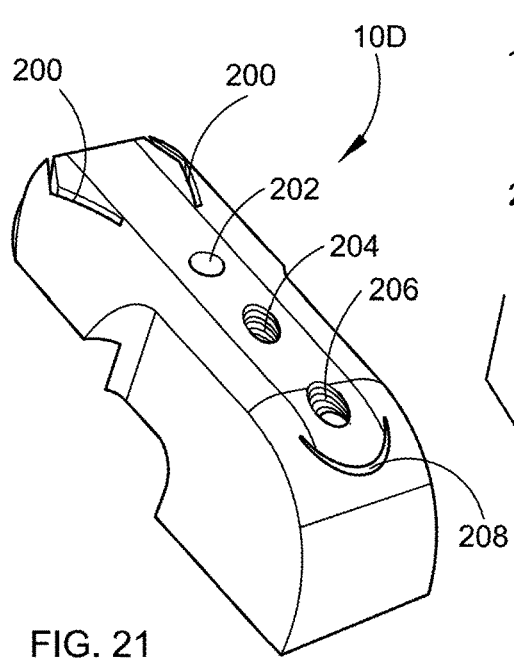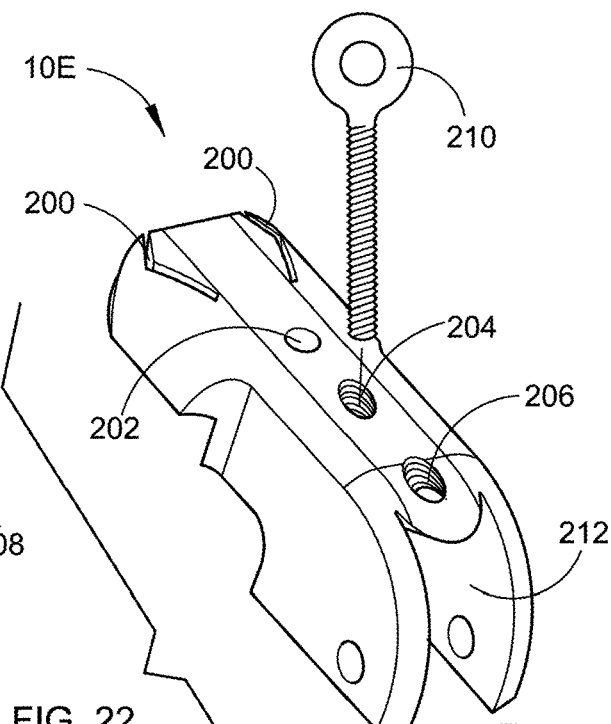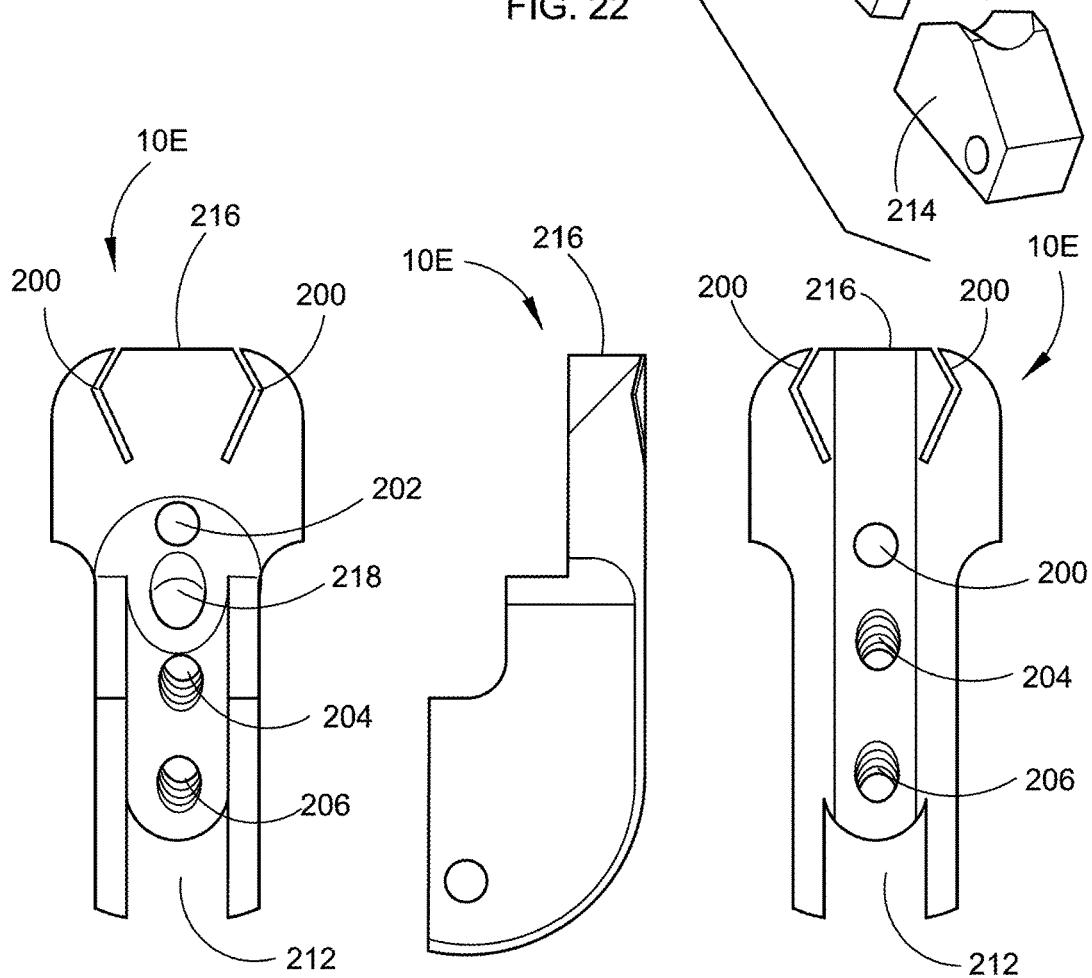
FIG. 21  FIG. 22  FIG. 23  FIG. 24  FIG. 25

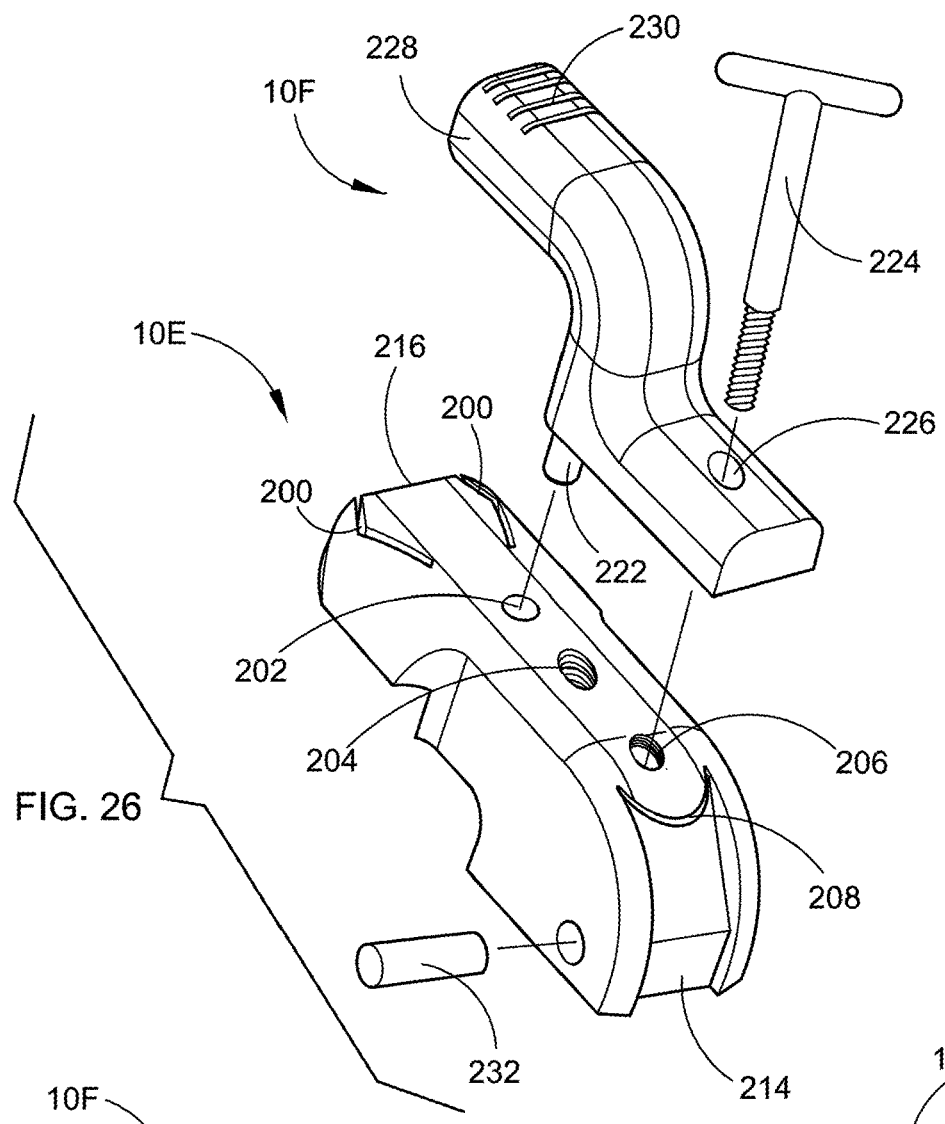
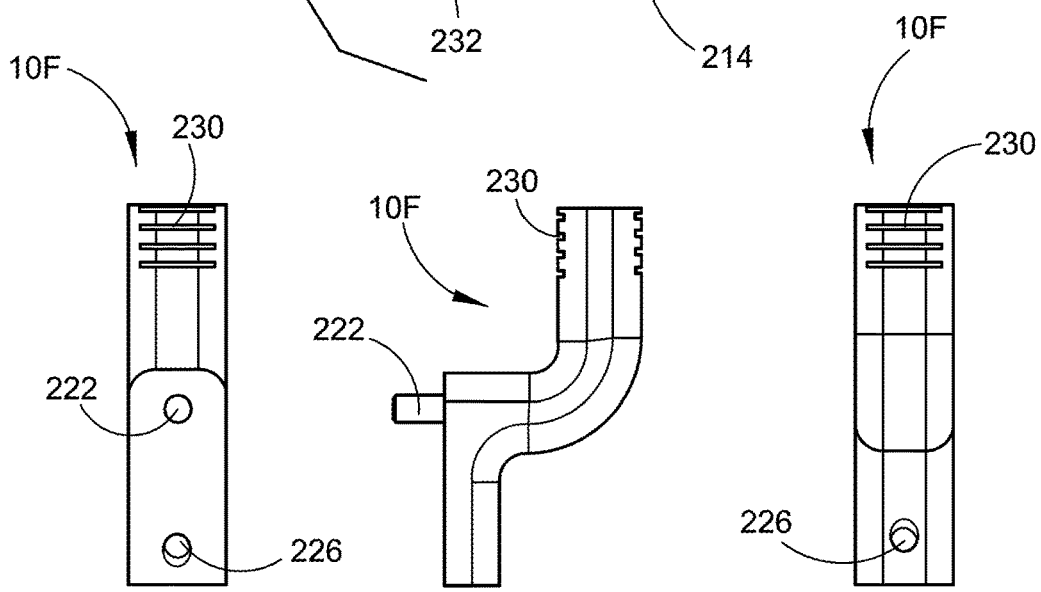
FIG. 27  FIG. 28  FIG. 29

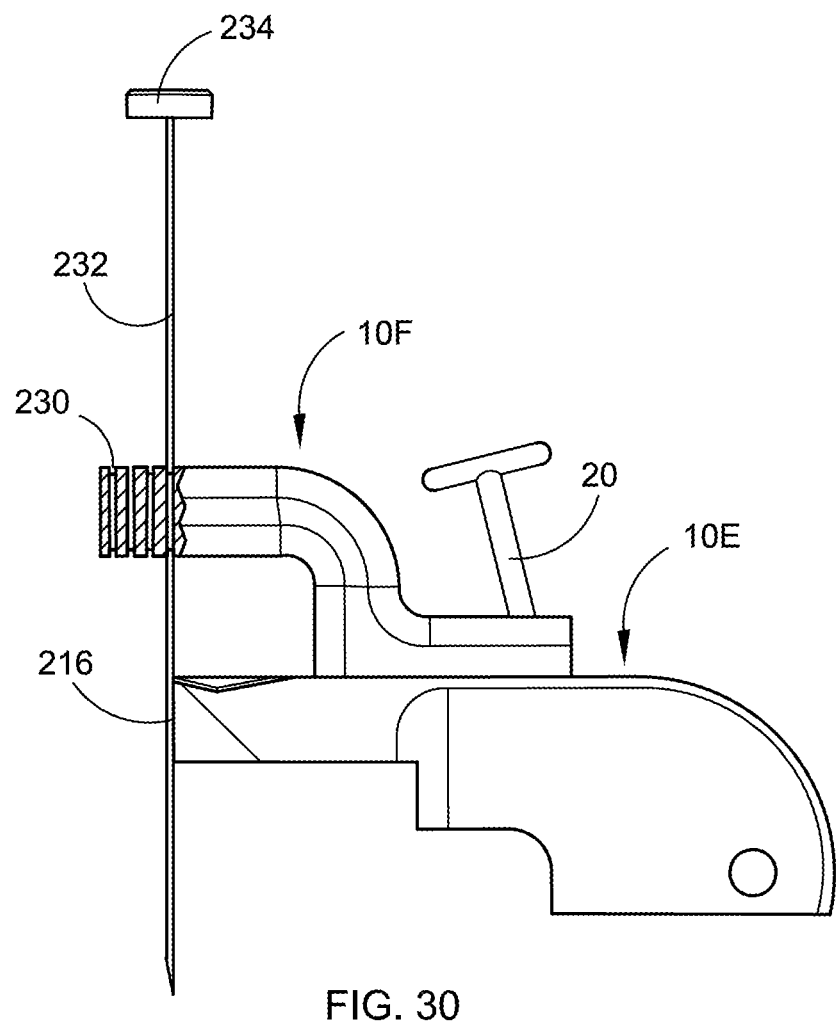
FIG. 30
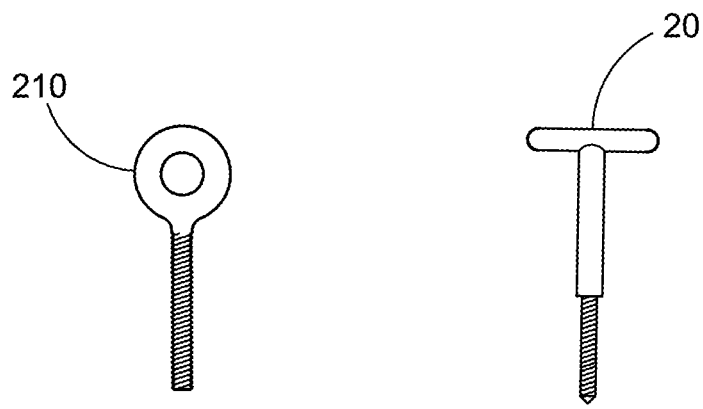
FIG. 31
FIG. 32

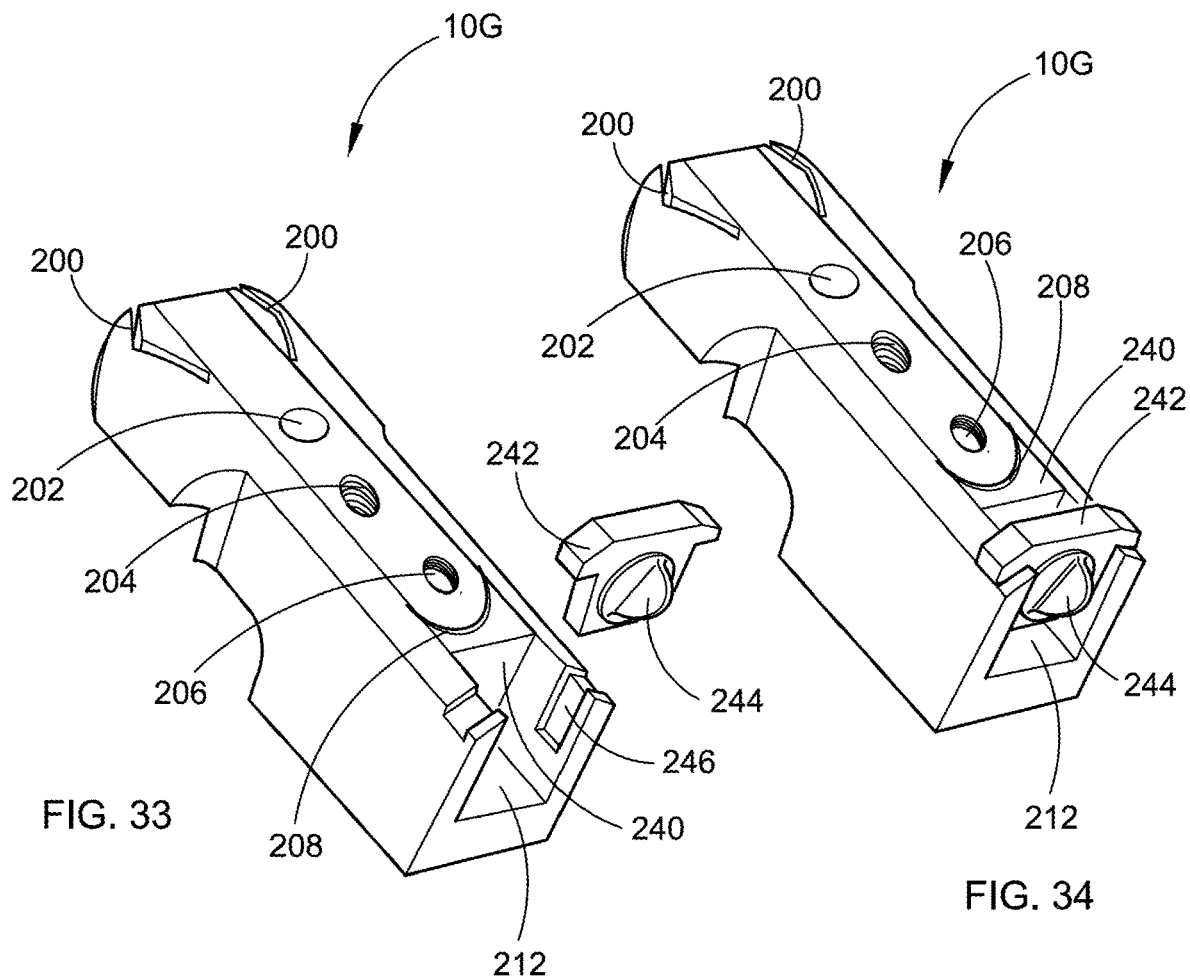
FIG. 33
FIG. 34
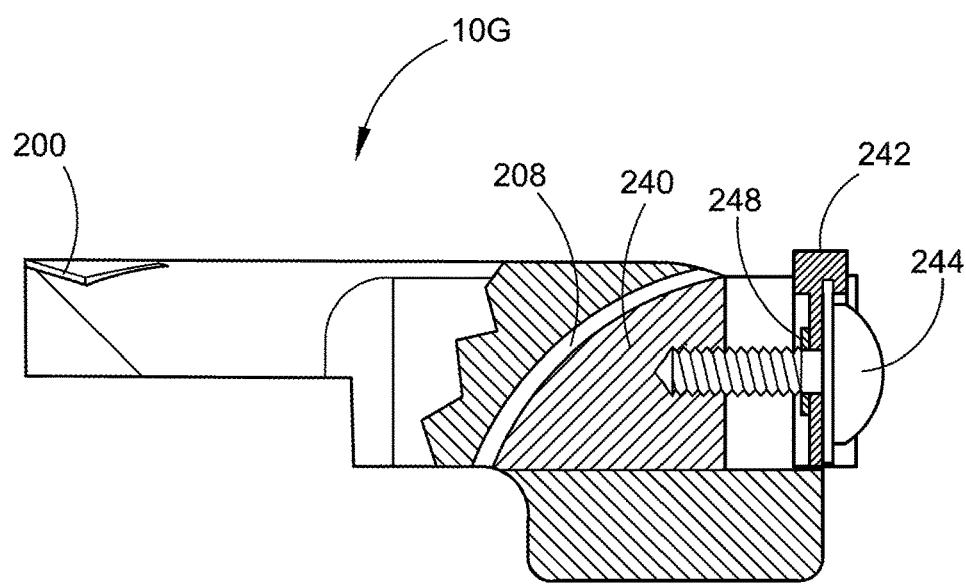
FIG. 35

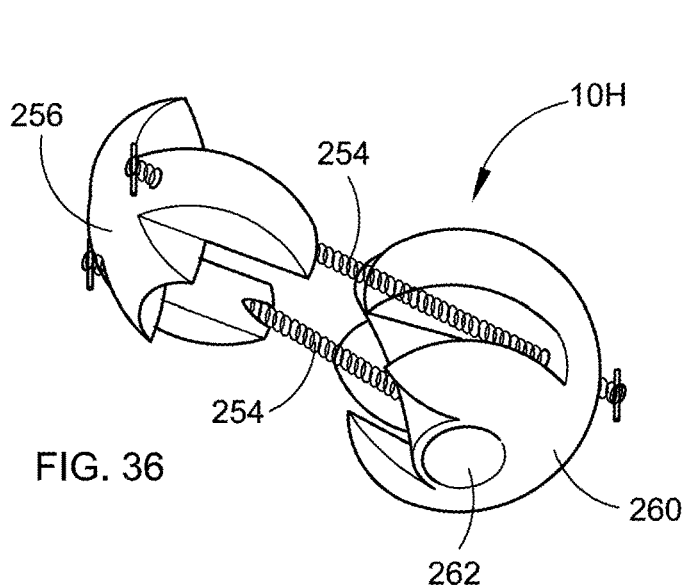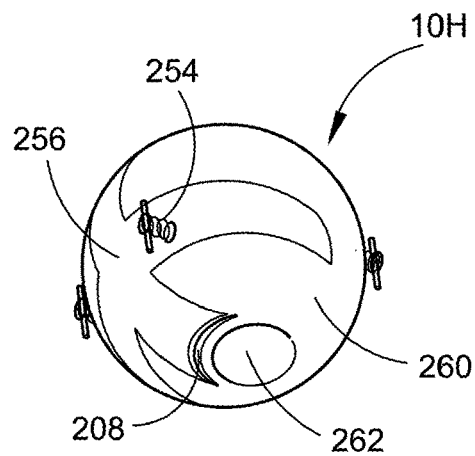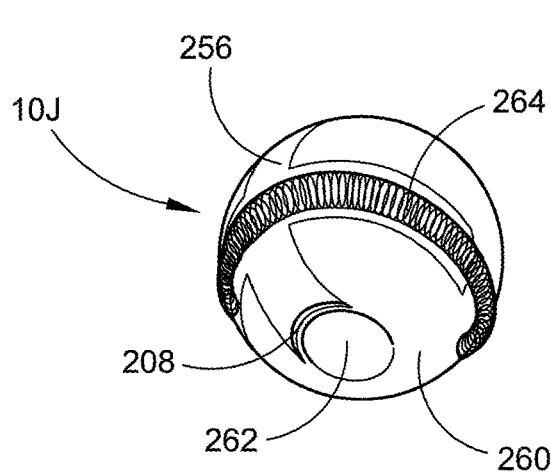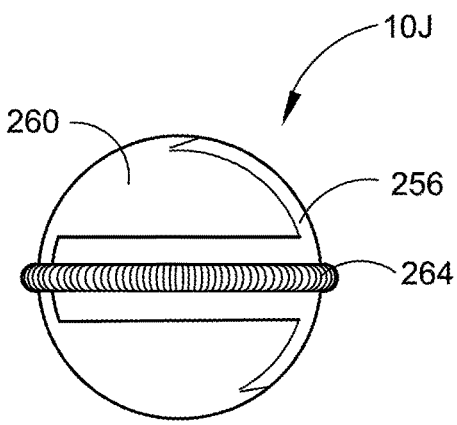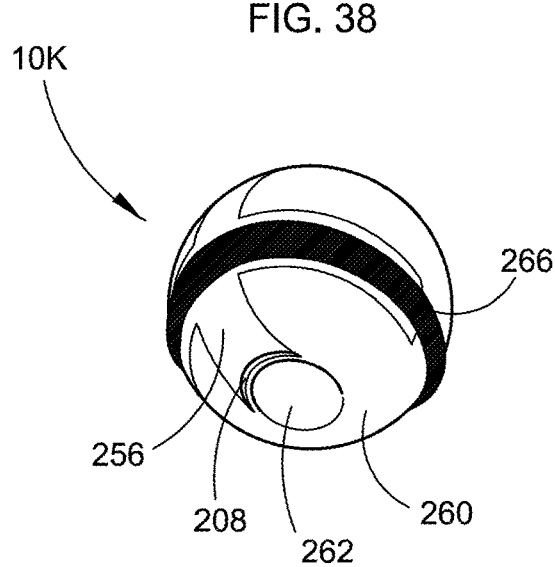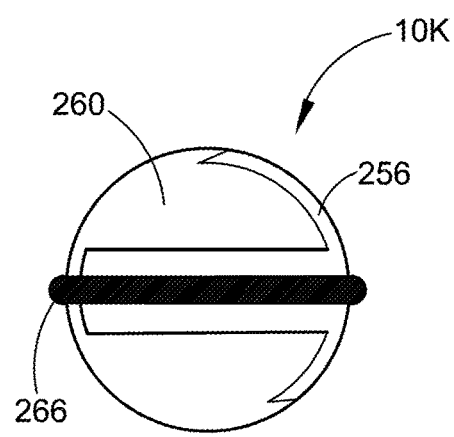
FIG. 36
FIG. 37
FIG. 38
FIG. 39
FIG. 40
FIG. 41

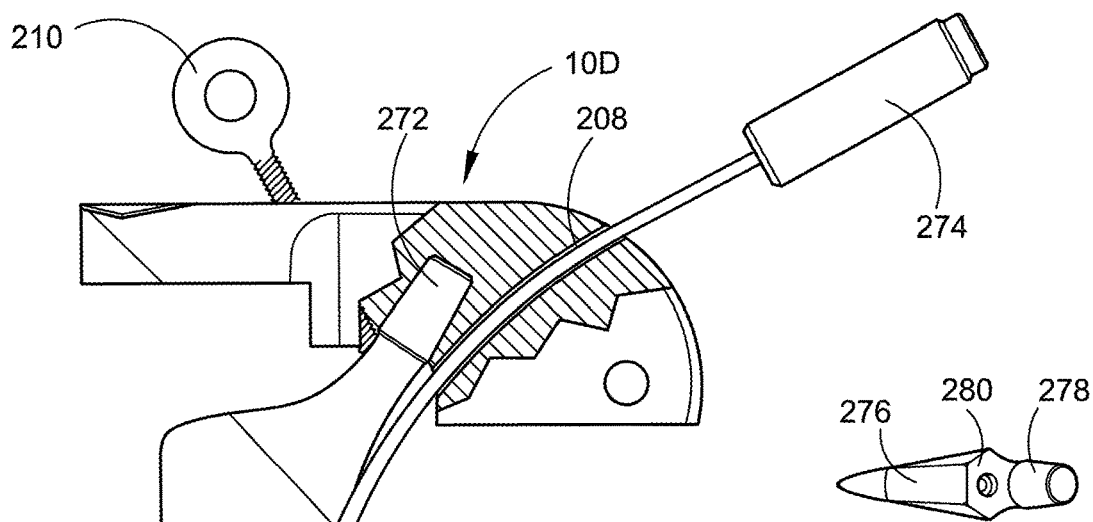
FIG. 44
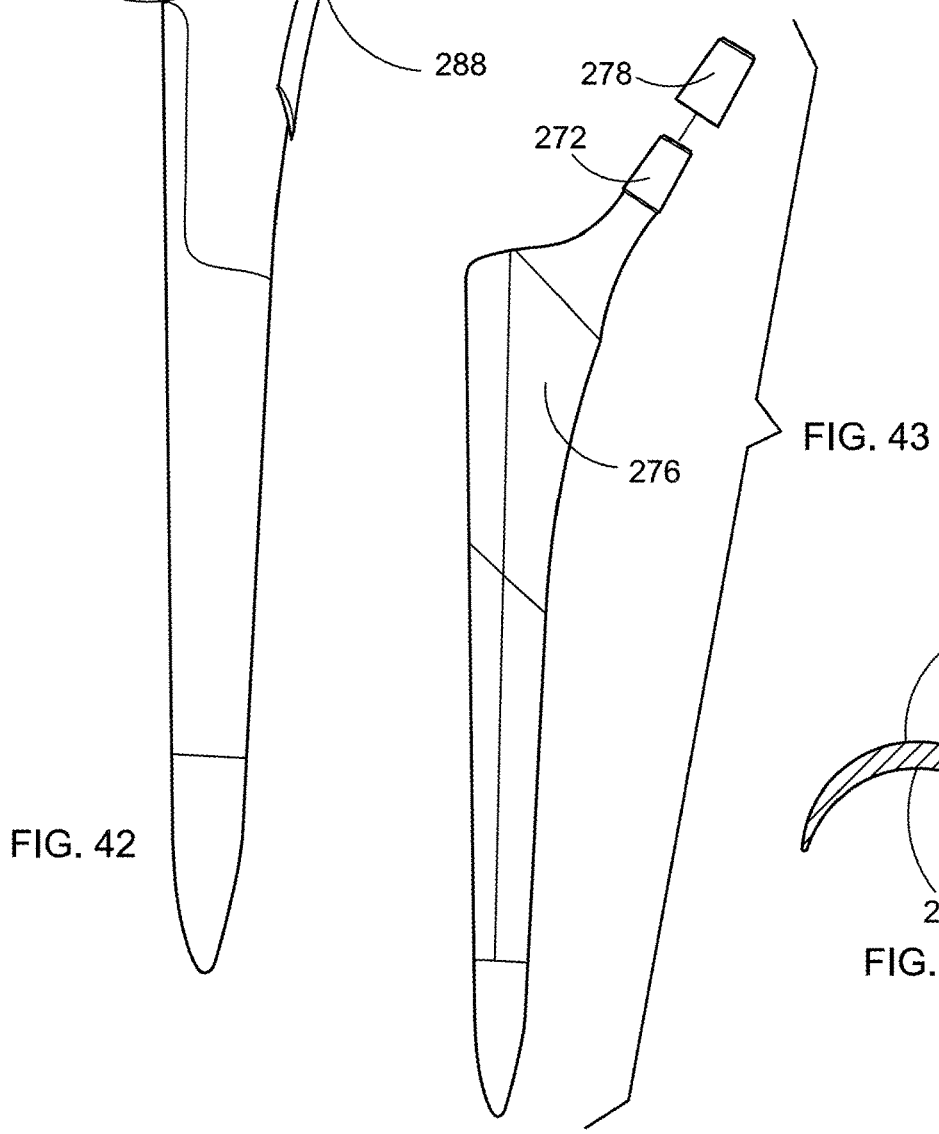
FIG. 42
FIG. 43
FIG. 45

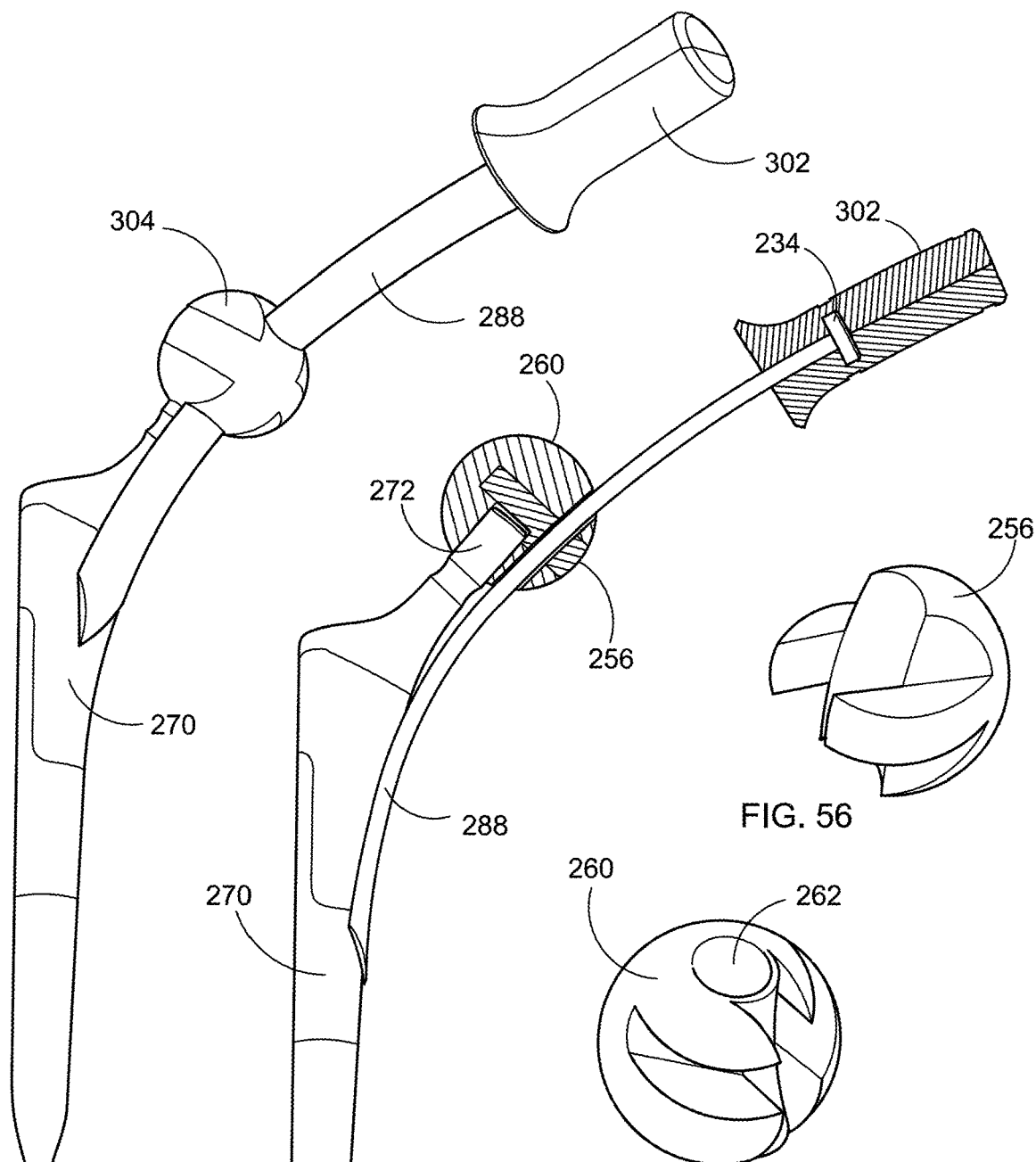
FIG. 54
FIG. 55
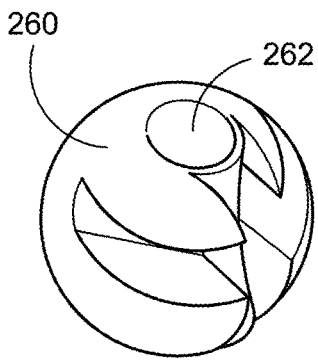
FIG. 57
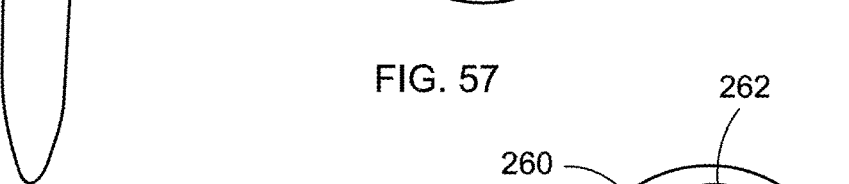
FIG. 56
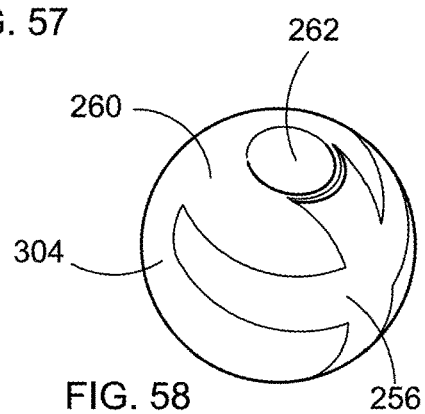
FIG. 58

JOINT REVISION SURGERY APPARATUS

FIELD OF THE INVENTION

This application relates to a surgical apparatus used on joint replacement revision surgery in the areas of the hip joint, shoulder joint and knee joint. More particularly, the present application is directed to a Joint Revision Surgery Apparatus includes a blade guide block frame which has a plurality of blade guide slots and a central cavity. The blade guide block central cavity is positioned over the trunnion end of the existing prosthesis to be removed and secured to the prothesis. Straight, curved and compound curved knife blades are guided by the blade guide slots to cut the prothesis free. The securing of the guide blade block support apparatus against the femur is accomplished by the means of a T handle screw or eyebolt threading into one of the threaded orifice in the blade guide block frame. The guide blocks in varying sizes and configurations, straight and curved knifes blades and related accessories may be sold as a complete kit. The Joint Revision Surgery Apparatus facilitates rapid, efficient and complete removal of an existing prosthesis during joint revision surgery.

BACKGROUND OF THE INVENTION

There is growing need to provide a new and refined method of performing delicate surgical operations including hip, shoulder and knee revisions. The similarity in these operations is that the implants have to be inserted into a major bone in the area and when there is a problem with them the prostheses has to be removed.

As with any other mechanical device, a total hip replacement can be subject to various forms of mechanical or biological failure. Such a failure may require a revision of the hip replacement to address the cause of failure and its consequences. A revision of a total hip replacement sometimes requires removal of the femoral implant.

The revision hip implant is comprised of four parts that work together to restore the original function of the ball-and-socket joint, namely, (1) A metal hip stem that is inserted into the top of the thighbone; (2) A metal cup which holds the cup liner; (3) A cup liner which holds the femoral head; and (4) The femoral head or ball which is attached to the top of the hip stem and is inserted into the cup liner to form the ball-and-socket joint.

The wearing down of the plastic component has an unfortunate side effect. The tiny plastic particles that wear off are attacked by your body's immune system, and this immune response also attacks the healthy bone around your implant. This leads to a condition called osteolysis, in which the bone in the area around the joint implant softens as it is absorbed by the body, thus making the implant unstable and in need of revision.

If the bone next to the primary implant is fractured in an accident, revision surgery may be required in order to provide a safe, stable joint. In this case, the original implant may need to be removed, the fracture addressed and a revision joint implanted.

In a low percentage of cases, the hip may become infected after surgery. Although it may be successfully treated with antibiotics, there are severe cases where a follow-up revision surgery may be required.

Hip revision operations are performed relatively infrequently. In the United States, there are approximately 18 revision hip replacements performed for every 100 hip replacements. The most common reasons for revision are: (1) Repetitive (recurrent) dislocation of a hip replacement; (2) Mechanical failure (implant wear and tear—loosening or breakage); and (3) infection.

Numerous, innovations for Joint Revision Surgery Apparatus have been provided in the prior art described as follows. Even though these innovations may be suitable for the specific individual purposes to which they address, they differ from the present Joint Revision Surgery Apparatus as hereinafter contrasted. The following is a summary of those prior art patents most relevant to the Joint Revision Surgery Apparatus at hand, as well as a description outlining the difference between the features of the present application and those of the prior art.

U.S. Pat. No. 9,138,242 of Randell J. Lewis describes a femoral hip stem explant system that has an alignment body which is attached to two locations of a femoral bone and has several lockable collet type adjustment features to set the shaft of a reamer or end mill exactly in coincidence with the femoral bone cavity axis. The shaft of the end mill or reamer is supported by a sleeve member, which is inserted into a drill guide central aperture. The drill guide aperture is adjusted first and locked to be in line with the femoral bone cavity. Each of the sleeve members has the same mating outer diameter, which fits into the drill guide central aperture. Accordingly, the sleeve members can be interchanged into the drill guide aperture With shafts of differently sized reamers or end mills.

This patent describes a femoral hip stem explant or revision system that has an alignment body which is attached to two locations of a femoral bone and has several lockable collet type adjustment features to set the shaft of a reamer or end mill exactly in coincidence with the femoral bone cavity axis. This patent describes a very invasive surgery to attach at two locations of a femoral bone where the Joint Revision Surgery Apparatus works from the top of the femur only and leaves the most proximal portion in fairly good shape.

U.S. Pat. No. 6,740,092 of Alan Lombardo et al. describes IM revision tools include reamers with depth markings or stops, an impactor-extractor with a coupling for attaching to tools which are inserted into and removed from the IM canal, a resection guide tower to which a cutting block is attached and which includes a notch which serves as both a witness mark and a holder for a femoral collar, a reversible clean-up cutting block with a quick-connect clamp attachable to the guide tower for resecting the distal femur, a selection of spacer blocks for measuring the space between the femur to determine the size of the components to be installed, a multiple cut cutting guide for preparing the femur, a set of 5 and 10 mm trial wedges, a trial stem valgus adapter, femoral sizing indicators which include indications of anterior/posterior offset, a stabilizer box cutting template which is attachable to the multiple cut cutting guide, and anterior/posterior offset adapters for attaching the femoral component to the IM stem.

This patent describes IM revision tools that include reamers with depth markings or stops, an impactor-extractor with a coupling for attaching to tools which are inserted into and removed from the IM canal, a resection guide tower to which a cutting block is attached. This patent describes a number of tools for positioning and alignment where the Joint Revision Surgery Apparatus uses the trunnion and the sides of the existing prostheses and the proximal portion of the femur for support and alignment of the process.

U.S. Pat. No. 6,258,095 of Alan Lombardo et al. describes IM revision tools include reamers with depth markings or stops, an impactor-extractor with a coupling for attaching to tools which are inserted into and removed from the IM canal, a resection guide tower to which a cutting block is attached and which includes a notch which serves as both a witness mark and a holder for a femoral or tibial collar, a reversible clean-up cutting block with a quick-connect clamp attachable to the guide tower for resecting the distal femur and separate left and right clean-up cutting blocks for resecting the proximal tibia, a selection of spacer blocks for measuring the space between the tibia and femur to determine the size of the components to be installed, a multiple cut cutting guide for preparing the femur, a set of 5 and 10 mm trial wedges, a trial stem valgus adapter, femoral sizing indicators which include indications of anterior/posterior offset, a stabilizer box cutting template which is attachable to the multiple cut cutting guide, and anterior/posterior offset adapters for attaching the femoral component to the IM stem. The tools according to the invention are modular and can also be used in primary knee arthrop tasty without 1M fixation. The methods of the invention provide accurate location of bone cuts so that the revision prosthetic is correctly oriented relative the IM canal and the bone cuts.

This is another patent that describes a number of tools for positioning and alignment where the Joint Revision Surgery Apparatus uses the trunnion and the sides of the existing prostheses and the proximal portion of the femur for support and alignment of the process.

US Patent Application Publication No. 2014/0371750 of Greg Klein et al. describes an apparatus for removal of a femoral implant that may include a handle portion and a cutting blade opposite the handle portion. The cutting blade may include a cutting edge, wherein the cutting edge includes a non-linear shape to substantially match at least a portion of a profile of the femoral implant to be removed.

This patent describes an apparatus for removal of a femoral implant that may include a handle portion and a cutting blade opposite the handle portion but does not describe the unique features of the Joint Revision Surgery Apparatus.

U.S. Pat. No. 9,282,981 of Rebecca L. Chaney describes a number of orthopedic surgical instruments for use in a surgical procedure to prepare a patient's femur to receive an orthopedic prosthesis are disclosed. The tools include guide tools, cutting tools, surgical blocks, and other orthopedic surgical instruments configured to plan and guide the preparation of the patient's femur.

This patent describes a number of orthopedic surgical instruments for use in a surgical procedure to prepare a patient's femur to receive an orthopedic prosthesis but does not describe unique features of the Joint Revision Surgery Apparatus.

None of the foregoing prior art teaches or suggests the particular unique features of the Joint Revision Surgery Apparatus and thus clarifies the need for further improvements in the devices that can be used for these purposes.

In this respect, before explaining at least one embodiment of the Joint Revision Surgery Apparatus detail, it is to be understood that the design is not limited in its application to the details of construction and to the arrangement of the components set forth in the following description or illustrated in the drawings. The Joint Revision Surgery Apparatuses disclosed herein are capable of other embodiments and of being practiced and carried out in various ways. Also, it is to be understood that the phraseology and terminology employed herein are for the purpose of description and should not be regarded as limiting.

SUMMARY OF THE INVENTION

The principle advantage of the of the Joint Revision Surgery Apparatus is to enable the performance of a significantly quicker, safer and more successful joint revision surgery procedure.

Another advantage of using the Joint Revision Surgery Apparatus is to have significantly less blood loss during the joint revision surgery procedure.

Another advantage of using the Joint Revision Surgery Apparatus is to have much shorter operating room use times during the joint revision surgery procedure.

Another advantage of using the Joint Revision Surgery Apparatus is to perform joint revision surgery with less instrumentation and tools, for example, cables and long stems during the procedure.

Another advantage of using the Joint Revision Surgery Apparatus is to have quicker times to have full weight bearing capability after joint revision surgery.

Another advantage of using the Joint Revision Surgery Apparatus is to have fewer complications during and after joint revision surgery.

Another advantage of using the Joint Revision Surgery Apparatus is to have less mortality following joint revision surgery.

Another advantage of using the Joint Revision Surgery Apparatus is to have less morbidity following joint revision surgery.

An advantage of the first alternate embodiment of the Joint Revision Surgery Apparatus is to have the internal elongated cavity allowing the upward movement of the existing prostheses.

Another advantage of using the first alternate embodiment of the Joint Revision Surgery Apparatus is by tightening the T handle screw, the existing prostheses can be moved upward.

Another advantage of using the first alternate embodiment of the Joint Revision Surgery Apparatus is by tightening the T handle screw to lift upwardly to extract the existing prostheses.

An advantage of the second alternate embodiment of the Joint Revision Surgery Apparatus is to have a simpler device to perform the joint revision surgery procedure.

The Joint Revision Surgery process entails the positioning of the support apparatus over the trunnion end of the existing prostheses within its internal cavity. The wide knife blades will initially be used to properly align the support apparatus with the side surfaces of the existing prostheses. The securing of the support apparatus down against the femur end is accomplished by the means of the T handle screw threading into the threaded orifice in of the existing prostheses.

Wide knife blades or shaped knife blades will be used to loosen both sides of the existing prostheses while narrow blades will be used around the tapered curved apertures and on the ends of the support apparatus. The distal end of one of the curved aperture has an internal curvature to guide the tapered knife blade along the curved front edge of the existing prostheses. The replaceable knives can be used in a pneumatic osteotome or tapped with a surgical hammer. Both the internally curved front edge and back edge of the existing prostheses may be flat or have a curved surface. The blades will be used with the sharp edge section toward the side surfaces of the existing prostheses to keep the knives from digging into or scraping the bone.

With respect to the above description then, it is to be realized that the optimum dimensional relationships for the parts of the Joint Revision Surgery Apparatus, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present design. Therefore, the foregoing is considered as illustrative only of the principles of the Joint Revision Surgery Apparatus. Further, since numerous modifications and changes will readily occur to those skilled in the art, it is not desired to limit the Joint Revision Surgery Apparatus to the exact construction and operation shown and described, and accordingly, all suitable modifications and equivalents may be resorted to, falling within the scope of this application.

While the apparatus and method has or will be described for the sake of grammatical fluidity with functional explanations, it is to be expressly understood that the claims, unless expressly formulated under 35 USC 112, or similar applicable law, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 USC 112 are to be accorded full statutory equivalents under 35 USC 112, or similar applicable law. The Joint Revision Surgery Apparatus can be better visualized by turning now to the following drawings wherein like elements are referenced by like numerals.

BRIEF DESCRIPTION OF THE DRAWINGS

The accompanying drawings, which are incorporated in and form a part of this specification, illustrate embodiments of the Joint Revision Surgery Apparatus and together with the description, serve to explain the principles of this application.

FIG. 1 depicts a cross section through the preferred embodiment of the support apparatus and tools used in performing the Joint Revision Surgery.

FIG. 2 depicts a side view of the hip replacement prostheses.

FIG. 3 depicts a narrow blade knife used in the Joint Revision Surgery.

FIG. 4 depicts a tapered blade knife used in the Joint Revision Surgery.

FIG. 5 depicts a wide blade knife used in the Joint Revision Surgery.

FIG. 6 depicts a side view of the T handle screw used in securing and removal of the existing prostheses.

FIG. 13 depicts a side view of the angled blade knife.

FIG. 14 depicts a side view of the wide blade knife.

FIG. 15 depicts a top view of the first alternate embodiment of the support apparatus.

FIG. 16 depicts a cross section through the first alternate embodiment of the support apparatus with the T head screw attached to the existing hip prosthesis.

FIG. 17 depicts a cross section through the first alternate embodiment of the support apparatus with angled blade knife or the wide blade knife along the sides of the existing prostheses and curved knives on the ends.

FIG. 18 depicts a cross section through the first alternate embodiment of the support apparatus where the T handle screw is tightened to pull the existing hip prosthesis up from the femur.

FIG. 21 depicts a perspective view of the third alternate embodiment of the blade guide block.

FIG. 22 depicts a perspective view of the fourth alternate embodiment of the blade guide block.

FIG. 23 depicts a bottom view of the fourth alternate embodiment of the blade guide block.

FIG. 24 depicts a side view of the fourth alternate embodiment of the blade guide block.

FIG. 25 depicts a top view of the fourth alternate embodiment of the blade guide block.

FIG. 26 depicts a perspective view of the fourth alternate embodiment of the blade guide block and the attaching secondary blade guide block.

FIG. 27 depicts the bottom view of the secondary blade guide block.

FIG. 28 depicts the side view of the secondary blade guide block.

FIG. 29 depicts the top view of the secondary blade guide block.

FIG. 30 depicts a side view of the fourth alternate embodiment of the blade guide block and the attaching secondary blade guide block connected with a flat blade going through one of the four slots in the end.

FIG. 31 depicts a front view of the eye bolt.

FIG. 32 depicts a front view of the T handle screw.

FIG. 33 depicts a perspective view of the fifth alternate embodiment of the blade guide block with the adjustable insert and the adjusting mechanism raised up.

FIG. 34 depicts a perspective view of the fifth alternate embodiment of the blade guide block with the adjustable insert and the adjusting mechanism in position.

FIG. 35 depicts a side cut-away view of the fifth alternate embodiment of the blade guide block with the adjustable insert and the adjusting mechanism.

FIG. 36 depicts a perspective view of the sixth alternate embodiment of the internal tension spring blade guide ball using an internal spring tensioner.

FIG. 37 depicts a side view of the sixth alternate embodiment of the external spring blade guide ball using an internal spring tensioner.

FIG. 38 depicts a perspective view of the sixth alternate embodiment of the blade guide ball using an external spring tensioner.

FIG. 39 depicts a side view of the seventh alternate embodiment of the blade guide ball using an external spring tensioner.

FIG. 40 depicts a perspective view of a two part eighth alternate embodiment of the blade guide ball with internal spring tensioners exposed.

FIG. 41 depicts perspective view of a two part eighth alternate embodiment of the blade guide ball with internal spring tensioners.

FIG. 42 depicts a side view of a prostheses attached to a cut-away third alternate embodiment of the blade guide block illustrating a thin curved blade with handle in position with the eye bolt secured against the prostheses trunnion.

FIG. 43 depicts a side view of a large prosthesis.

FIG. 44 depicts a side view of a small prostheses with a trunnion adapter extended away from it.

FIG. 45 depicts a top view of the small prostheses illustrating the semi-hexagonal shape.

FIG. 54 depicts a perspective view of a typical prosthesis with a two part blade guide ball and a two part handle.

FIG. 55 depicts side view of a typical prosthesis with a two part blade guide ball and a two part handle with the metal end cap enclosed.

FIG. 56 depicts a perspective view of the insert section of the two part blade guide ball.

FIG. 57 depicts a perspective view of the base section of the two part blade guide ball.

FIG. 58 depicts a perspective view of the two part blade guide ball.

DETAILED DESCRIPTION OF THE PREFERRED EMBODIMENTS

Figure 7:
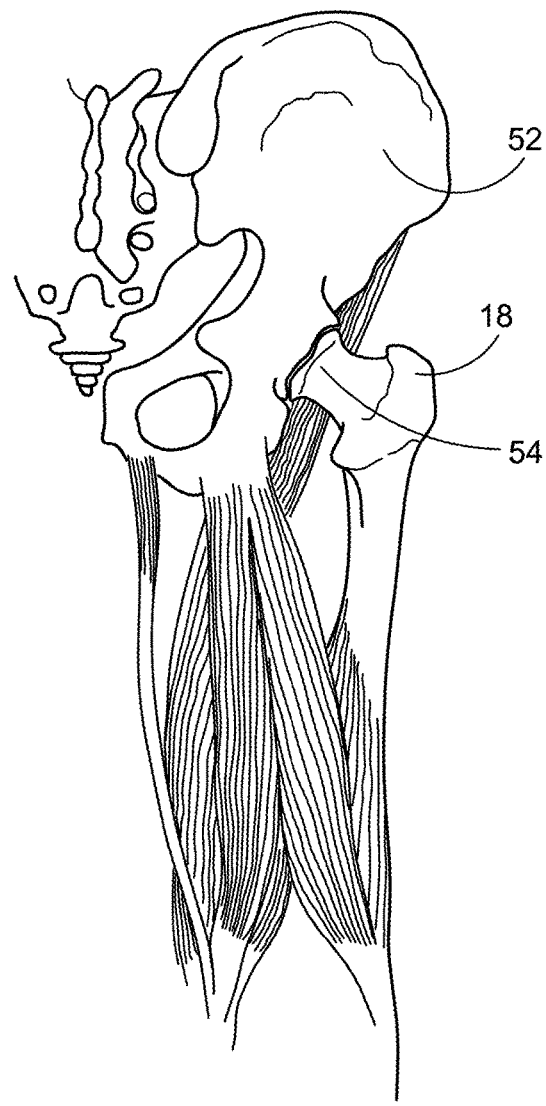
FIG. 7 depicts a view of a normal hip illustrating the pelvis, and femur connection.

As required, the detailed embodiments of the present Joint Revision Surgery Apparatus 10A, 10B, 10C, 10D, 10E, 10F, 10G, 1OH, 10J are disclosed herein, however, it is to be understood that the disclosed embodiments are merely exemplary of the design that may be embodied in various forms. Therefore, specific functional and structural details disclosed herein are not to be interpreted as limiting, but merely as basic for the claims and as a representative basis for teaching one skilled in the art to variously employ the present design in virtually any appropriately detailed structure.

FIG. 1 depicts a cross section through the preferred embodiment of the support apparatus 10A and tools used in performing the Joint Revision Surgery. The process entails the positioning of the support apparatus 12A over the trunnion end 14 of the existing prostheses 16 within its internal cavity 17. The wide knife blades 24 will initially be used to properly align the support apparatus 12A with the side surfaces 42 of the existing prostheses 16. Then, securing the support apparatus 12A down against the femur end 18 by the means of the male threaded T handle screw 20 that threads into the female threaded orifice 22 in the existing prostheses 16.

Wide knife blades 24 or shaped knife blades 26 will be used to loosen both sides of the existing prostheses 16 while narrow blades 28 will be used around the tapered curved apertures 30 and 31 on the ends of the support apparatus 12A. The distal end of the curved aperture 31 has an internal curvature 32 to guide the tapered knife blade 28 along the curved front edge 34 of the existing prostheses 16. The replaceable knives can be used in a pneumatic osteotome 36 or tapped with a surgical hammer. Both the internally curved front edge 34 and back edge 38 of the existing prostheses 16 may be a flat or have a curved surface.

FIG. 2 depicts a side view of the hip replacement prostheses 40 with the trunnion end 14 and the lower stem portion 44. A threaded existing orifice 46 is located on the exposed shoulder 48.

FIG. 3 depicts a narrow blade knife 28 used in the Joint Revision Surgery. The blades will be used with the sharp edge 76 section away from the side surfaces 78 of the existing prostheses 16 to keep the knives from digging into or scraping the metal.

FIG. 4 depicts a shaped blade knife 26 used in the Joint Revision Surgery.

FIG. 5 depicts a wide blade knife 24 used in the Joint Revision Surgery,

FIG. 6 depicts a side view of the male threaded T handle screw 20 used in securing and removal of the existing prostheses 16.

FIG. 7 depicts a view of a normal hip illustrating the pelvis 52, and femur end 18 connection to the pelvis 52.

Figure 8:
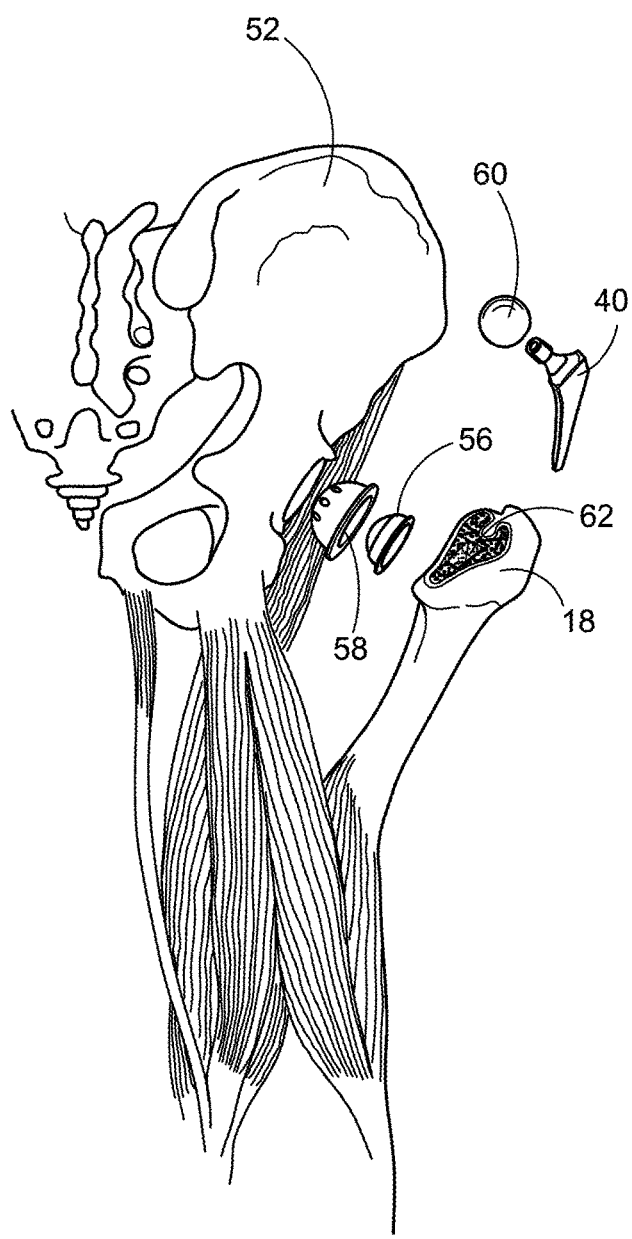
FIG. 8 depicts a view of the femur separated from the pelvis with the existing ball section removed and the plastic cup and metal shell exploded away. The existing hip prosthesis and ball are above the existing cavity.

FIG. 8 depicts a view of the femur end 18 separated from the pelvis 52 with the existing ball section 54 removed and the plastic cup 56 and metal shell 58 exploded away. The hip replacement prosthesis 40 and replacement ball 60 are above the existing cavity 62 in the femur end 18.

Figure 9:
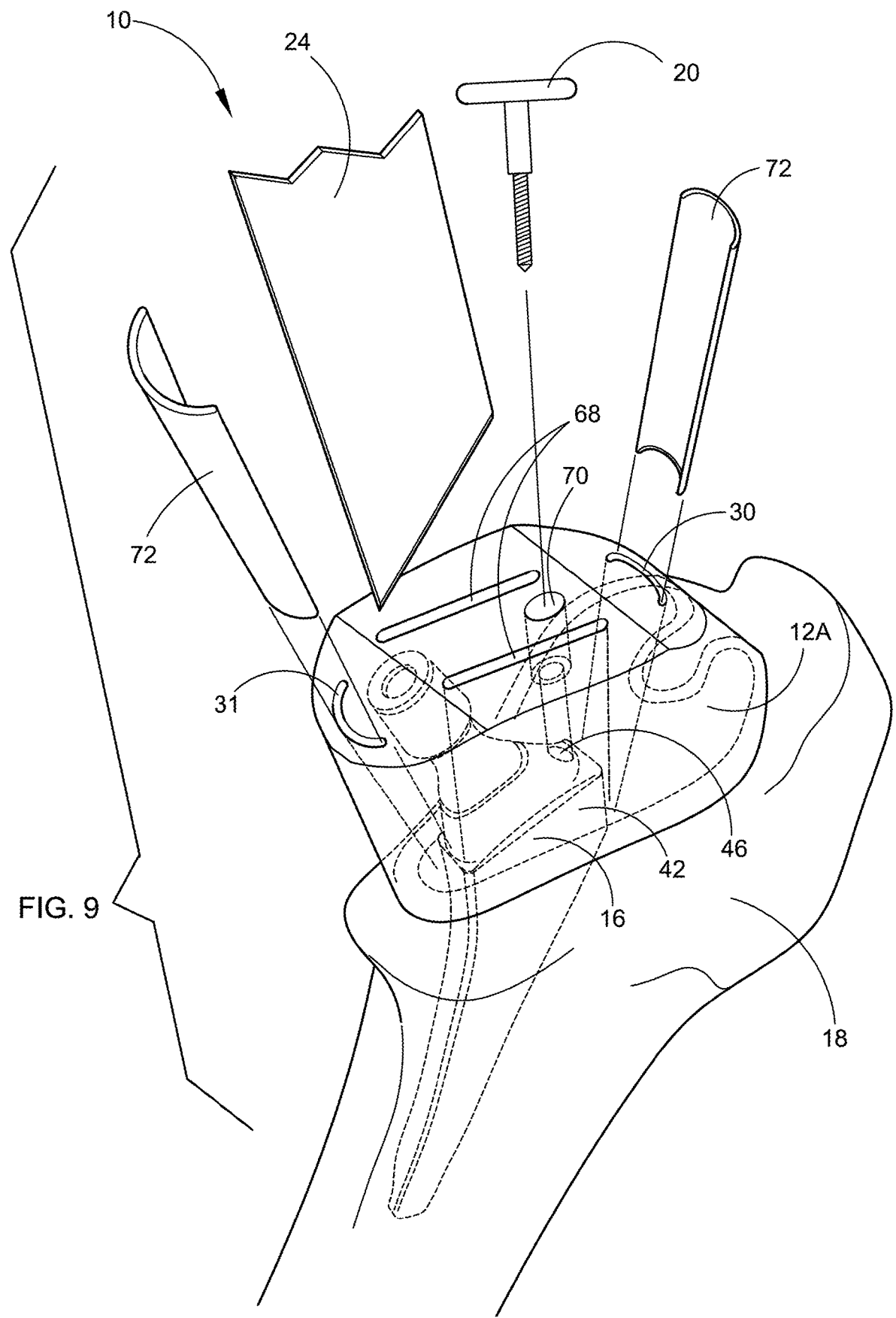
FIG. 9 depicts a perspective view of the femur end with the support apparatus in place.

FIG. 9 depicts a perspective view of the femur end 18 with the support apparatus 12A in place. One of the wide knife blades 24 is positioned above one of the two tapered guide slots 68 that extend to the side surfaces 42 of the existing prostheses 16. The male threaded T handle screw 20 is shown above the orifice 70 in the support apparatus 12A that extends to the existing female threaded orifice 46 in the existing prostheses 16. Two optional curved knives 72 are illustrated above the tapered curved slots 74 in the support apparatus 12A.

Figures 10, 11:
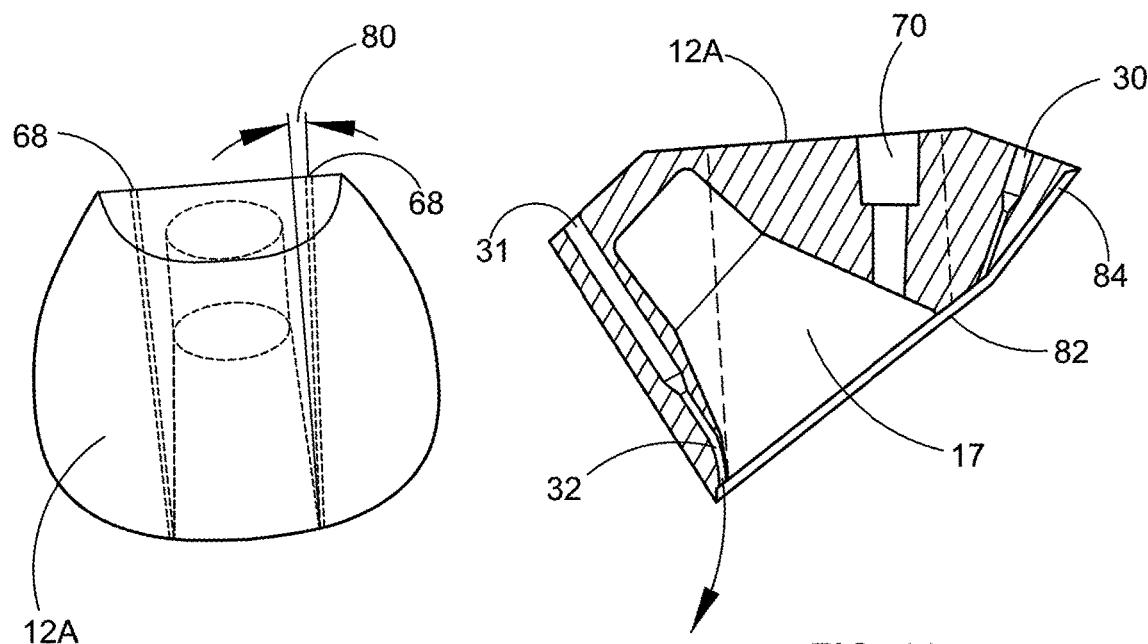
FIG. 10 depicts an end view of the preferred embodiment of the support apparatus.
FIG. 11 depicts a side view cross section of the preferred embodiment of the support apparatus.

FIG. 10 depicts an end view of the preferred embodiment of the support apparatus 12A illustrating the angles 80 of the tapered slots 68.

FIG. 11 depicts a side view cross section of the preferred embodiment of the support apparatus 12A illustrating the internal cavity 17 the tapered curved aperture 30 and the tapered curved aperture 31 with the internal curvature 32 at the distal end. The bottom surface 82 of the support apparatus 12A will have an internally beveled edge 84 on its perimeter.

Figure 12:
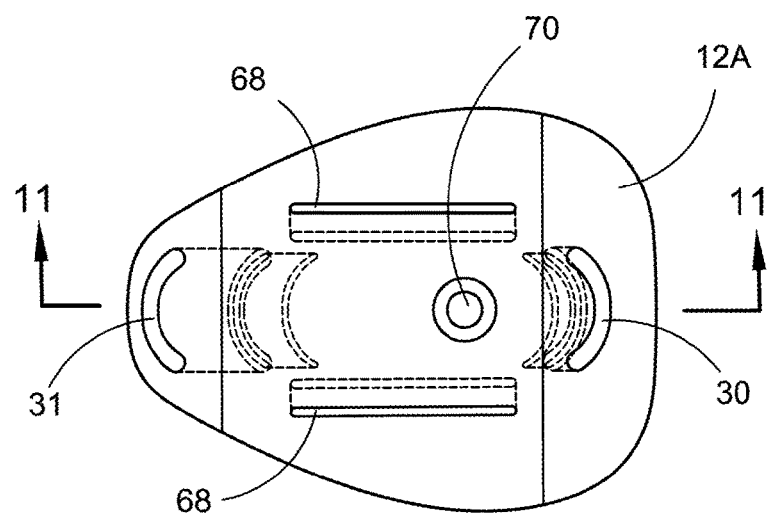
FIG. 12 depicts a top view of the preferred embodiment of the support apparatus.

FIG. 12 depicts atop view of the preferred embodiment of the support apparatus 12A illustrating the tapered curved aperture 30 and the tapered curved aperture 31 with the internal curvature 32 at the distal end, the two tapered guide slots 68 and the orifice for the "T" handle screw 20.

FIG. 13 depicts a side view of the angled blade flat knife 86 to be used on the first alternate embodiment of the support apparatus 12B.

FIG. 14 depicts a side view of the wide blade knife 88 to be used on the first alternate embodiment of the support apparatus 12B.

FIG. 15 depicts a top view of the first alternate embodiment of the support apparatus 10B with support apparatus 12B having an elongated orifice 90 at the top of the enlarged internal elongated cavity 92. The cavity has been elongated to the back side to allow the existing prostheses 16 to only move back and up when the T head screw 20 is tightened to extract the device.

FIG. 16 depicts a cross section through the first alternate embodiment of the of the support apparatus 10B with the T head screw 20 attached to the existing prosthesis 16 and the wide blade knife 88 is inserted in one of the tapered guide slots 68 to align the support apparatus 12B in position on the existing prosthesis 16.

FIG. 17 depicts a cross section through the first alternate embodiment of the support apparatus 10B with angled blade knife 86 or the wide blade knife 88 inserted along the sides of the existing prostheses 16 and curved knives 72 on the ends.

FIG. 18 depicts a cross section through the first alternate embodiment of the support apparatus 10B where the T handle screw 20 is tightened to pull the existing prosthesis 16 up from the femur end 18. If necessary, the T handle screw 20 can be partially backed out of the existing prosthesis 16 and can be moved up and down to further release the adhesive bond on the device.

Figure 19:
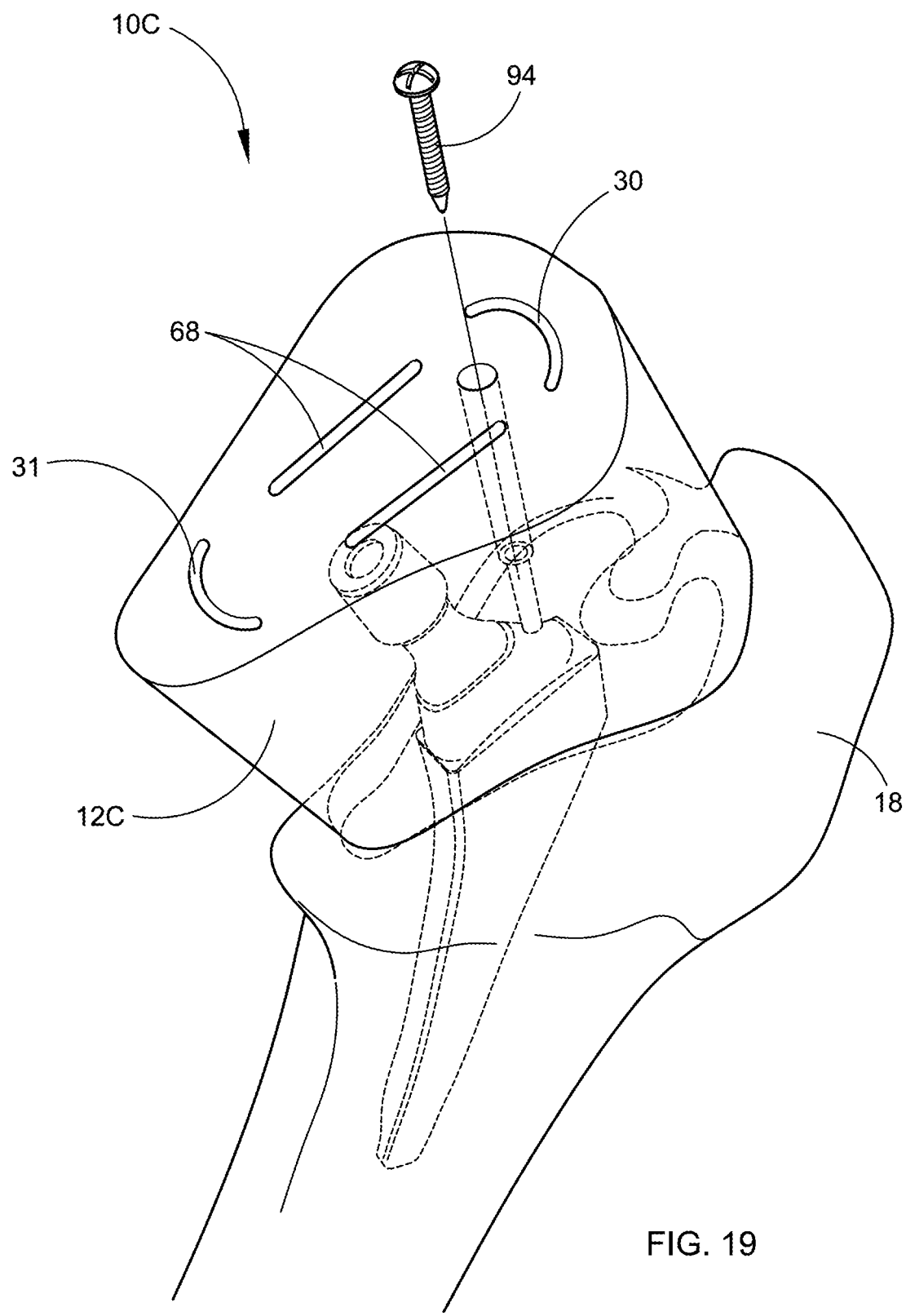
FIG. 19 depicts a perspective view of the second alternate embodiment of the support apparatus with a different configuration.

FIG. 19 depicts a perspective view of the second alternate embodiment of the support apparatus 10C with a different simpler configuration of the support apparatus 12C with two tapered guide slots 68, the tapered curved aperture 30 and tapered aperture 31 with the internal curvature 32 in the distal end. A conventional style of male threaded set screw 94 will be used to secure the support apparatus 10C in place over the femur end 18.

Figure 20:
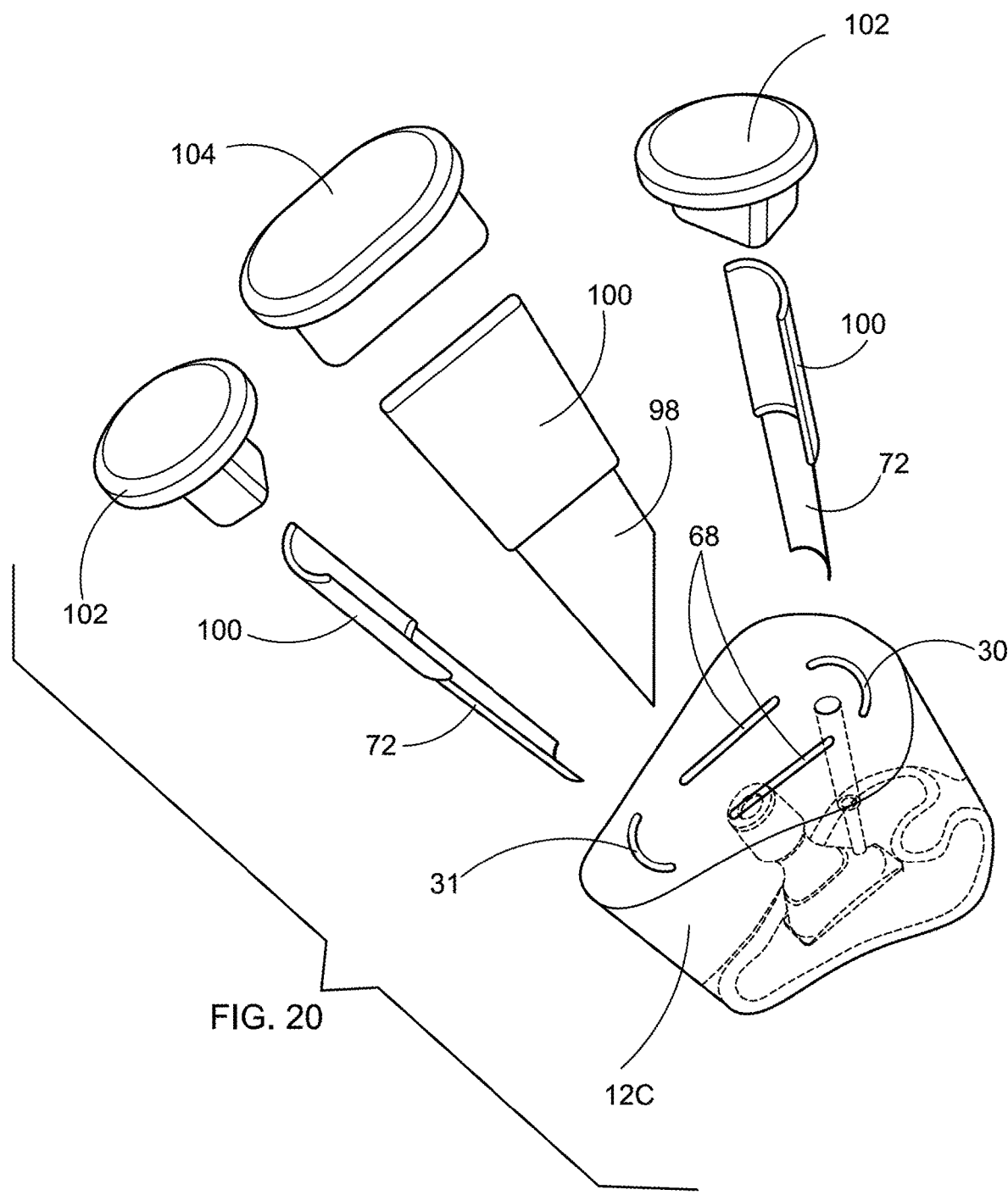
FIG. 20 depicts a perspective view of the second alternate embodiment of the support apparatus with a different configuration illustrating the tools used in the procedure.

FIG. 20 depicts a perspective view of the second alternate embodiment of the support apparatus 10C with the different simpler configuration of the support apparatus 12C illustrating the tools used in the procedure. A wide blade knife 98 with a depth restricting section 100 can be used with the pneumatic osteotome 36 or tapped with a surgical hammer Two optional curved blades 72 may be used in the tapered curved aperture 30 and tapered aperture 31 with the internal curvature 32. Two small blade adapters 102 and one large blade adapter 104 will fit over the top of the blades when they are used by hand pressure or tapped with a surgical hammer.

FIG. 21 depicts a perspective view of the third alternate embodiment of the one-piece blade guide block 10D illustrating the locations of the angular blade slots 200, the smooth alignment orifice 202, the female threaded angled eye bolt orifice 204 and the female threaded securing orifice 206 along with the curved blade cavity 208. This one-piece guide blade block 10D could be constructed of stainless steel, composite materials or hard plastic.

FIG. 22 depicts a perspective view of the fourth alternate embodiment of the two-piece blade guide block 10E illustrating the locations of the angular blade slots 200, the smooth alignment orifice 202, the female threaded angled eye bolt orifice 204 and the female threaded securing orifice 206 and the insert cavity 212 with the insert 214 moved away, along with the curved blade cavity 208 with the male threaded eye bolt 210 raised above and the insert cavity 212. This two-piece guide blade block 10E could be constructed of stainless steel, composite materials or hard plastic.

FIG. 23 depicts a bottom view of the fourth alternate embodiment of the blade guide block 10E detailing the bottom view with angular blade slots 200, the smooth alignment orifice 202, the threaded angled eye bolt orifice 204 and the threaded securing orifice 206 along with the curved blade cavity 208 with the insert cavity 212 and the flat front blade guide surface 216. The prosthesis tninnion cavity 218 does not fully penetrate completely through the device.

FIG. 24 depicts a side view of the fourth alternate embodiment of the blade guide block 10E illustrating the flat front blade guide surface 216.

FIG. 25 depicts a top view of the fourth alternate embodiment of the blade guide block 10E detailing the top view with angular blade slots 200, the smooth alignment orifice 202, the female threaded angled eye bolt orifice 204 and the female threaded securing orifice 206 along with the curved blade cavity 208 with the insert cavity 212 and the flat front blade guide surface 216.

FIG. 26 depicts a perspective view of the fourth alternate embodiment of the two-piece blade guide block 10E with a secondary handle-shaped guide block 10F, illustrating the top view with angular blade slots 200, the smooth alignment orifice 202, the female threaded angled eye bolt orifice 204 and the female threaded securing orifice 206 along with the curved blade cavity 208 with the insert 212 cavity and the flat front blade guide surface 216. The attaching secondary blade guide block 10F is shown raised up illustrating the location of the locating dowel 222 that mates with the smooth alignment orifice 202 and the male threaded T-screw 224 goes through the orifice 226 in the secondary blade guide block 10F and into the female threaded securing orifice 206. The distal end 228 of the secondary blade guide block 10F is shown with four slots 230 that will align with the flat front blade guide surface 216 of the blade guide block 10E for different styles of prosthesis. The dowel 232 when inserted allows the insert 214 to move slightly keeping it from binding with the different knife blades.

FIG. 27 depicts the bottom view of the secondary blade guide block 10F showing the four slots 230 the end of the locating dowel 222 and the orifice 226.

FIG. 28 depicts the side view of the secondary blade guide block 10F showing the four slots 230 the end of the locating dowel 222.

FIG. 29 depicts the top view of the secondary blade guide block 10F showing the four slots 230 and the orifice 226.

FIG. 30 depicts a side view of the fourth alternate embodiment of the blade guide block 10E with the attached secondary blade guide block 10F with the male threaded T handle screw 20 and a flat knife blade 232 with the upper metal cap end 234 extending through one of the slots 230 located in the secondary blade guide block 10F.

FIG. 31 depicts a front view of the male threaded eye bolt 210.

FIG. 32 depicts a front view of the male threaded T handle screw 20.

FIG. 33 depicts a perspective view of the fifth alternate embodiment of the blade guide block 10G with angular blade slots 200, the smooth alignment orifice 202, the female threaded angled eye bolt orifice 204, the threaded securing orifice 206 and the curved blade cavity 208. The insert 212 cavity with the adjustable insert 240 and the adjusting mechanism 242 has a pressure adjustment knob 244 shown raised up. The adjusting mechanism 242 can be slid down through grooves 246 on either side of the insert cavity 212 in the blade guide block 10G to be able to move the adjustable insert 240 forward and backward.

FIG. 34 depicts a perspective view of the fifth alternate embodiment of the blade guide block 10G with the adjustable insert 240 in the insert cavity 212 and the adjusting mechanism 242 in position.

FIG. 35 depicts a side cut-away view of the fifth alternate embodiment of the blade guide block 10G with the adjustable insert 240 and the adjusting mechanism 242. The pressure adjustment knob 244 is secured in place in the adjusting mechanism 242 by the means of a snap ring 248 so that when the pressure adjustment knob 244 is rotated the adjustable insert 240 can move forward and backward, to be able to put a light pressure on a blade within the curved blade cavity 208.

FIG. 36 depicts a perspective view of the sixth alternate embodiment of the internal tension spring blade guide ball 10H using an internal spring tensioner 254 to restrain the female guide ball section 256 to the male guide ball section 260 that has the prosthesis trunnion orifice 262 at the bottom.

FIG. 37 depicts a side view of the sixth alternate embodiment of the external spring blade guide ball 10H using an internal spring tensioner 254 to restrain the female guide ball section 256 to the male guide ball section 260 that has the prosthesis trunnion orifice 262 at the bottom.

FIG. 38 depicts a perspective view of the sixth alternate embodiment of the blade guide ball 10J using an external spring tensioner 264 to restrain the female guide ball section 256 to the male guide ball section 260 to restrain the female guide ball section 256 to the male guide ball section 260 that has the prosthesis trunnion orifice 262 at the bottom.

FIG. 39 depicts a side view of the seventh alternate embodiment of the blade guide ball 10J using an external spring tensioner 264 to restrain the female guide ball section 256 to the male guide ball section 260.

FIG. 40 depicts a perspective view of a two part eighth alternate embodiment of the blade guide ball 10K with an external elastic tensioner 266 to restrain the female guide ball section 256 to the male guide ball section 260 that has the prosthesis trunnion orifice 262 at the bottom.

FIG. 41 depicts a side view of a two part eighth alternate embodiment of the blade guide ball 10K with an external elastic tensioner 266 to restrain the female guide ball section 256 to the male guide ball section 260.

FIG. 42 depicts a side view of a large prostheses 270 attached to a cut-away third alternate embodiment of the basic blade guide block 10D illustrating a thin curved blade with straight handle 274 in the compound curved prosthesis blade 288 and a curved handle 274 cavity 208 with the male threaded eye bolt 210 secured tightly against the prostheses trunnion 272 to aide in the extraction of the prosthesis.

FIG. 43 depicts a side view of a small prosthesis 276 having the trunnion 272 and the trunnion size adaptor 278 which fits over the prostheses trunnion 272 to add thickness to the prostheses trunnion 272 for a better fit with the blade guide block used in the revision surgery procedure.

FIG. 44 depicts a top view of the small prostheses 276 illustrating the semi-hexagonal shape 280 of the upper section of the small prostheses 276 that conforms to the angular slots 200 in the blade guide blocks 10D, 10E and 10G. Different sizes are anticipated to accommodate differing sizes of implanted stems undergoing revision surgery.

FIG. 45 depicts a cross section through a compound curved prosthesis blade 288 where the inner surface 290 conforms to the shape of the typical prosthesis radius and the length of the typical blade has a sweeping curve to it.

Figure 46:
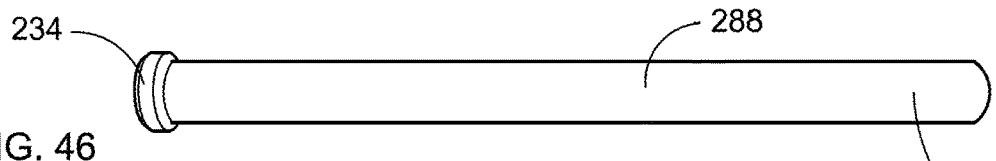
FIG. 46 depicts a top view of a heavy curved blade a curved, sharp end and a metal end cap.

FIG. 46 depicts a top view of a heavy compound curved prosthesis 288 with a curved sharp end 218 and a metal end cap 234.

Figure 47:
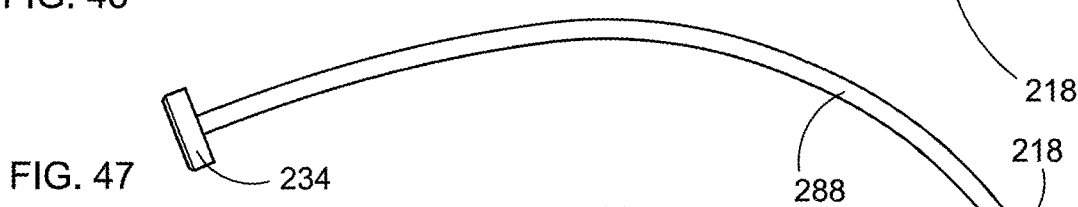
FIG. 47 depicts a side view of a heavy curved blade a curved sharp end and a metal end cap.

FIG. 47 depicts a side view of a heavy compound curved prosthesis blade 288 a curved sharp end 218 and a metal end cap 234.

Figure 48:
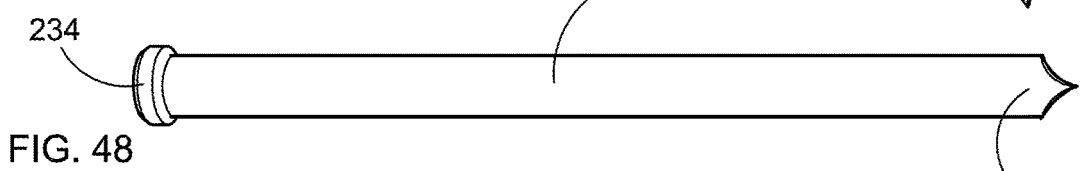
FIG. 48 depicts a top view of a thin curved blade a curved sharp end and a metal end cap.

FIG. 48 depicts a top view of a thin compound curved prosthesis blade 288 with a curved sharp pointed end 292 and a metal end cap 234.

Figure 49:
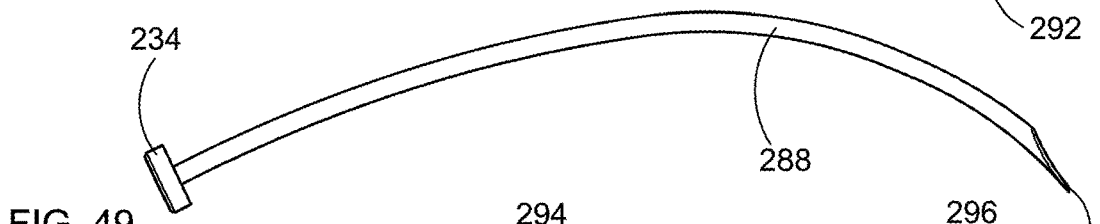
FIG. 49 depicts a side view of a thin curved blade a curved sharp pointed end and a metal end cap.

FIG. 49 depicts a side view of a thin compound curved prosthesis blade 288 with a curved sharp pointed end 292 and a metal end cap 234.

Figure 50:
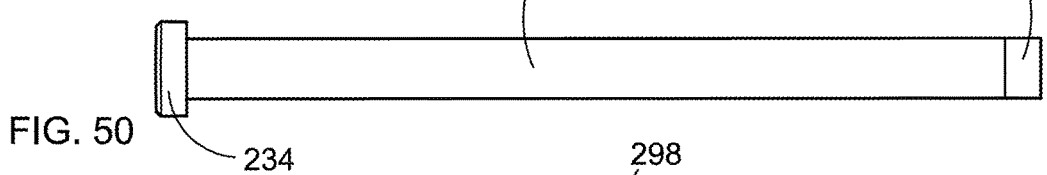
FIG. 50 depicts a top view of a straight narrow flat blade with a chisel shaped sharp end and a metal end cap.

FIG. 50 depicts a top view of a straight narrow flat blade 294 with a chisel shaped sharp end 296 and a metal end cap 234.

Figure 51:
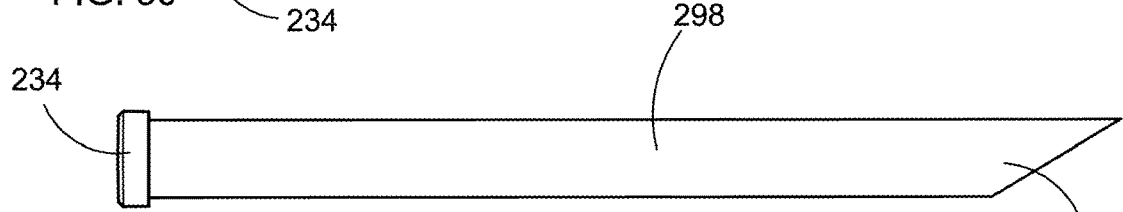
FIG. 51 depicts a top view of a straight wide flat blade with a triangular shaped sharp end and a metal end cap.

FIG. 51 depicts a top view of a straight wide flat blade 298 with a triangular shaped sharp end 300 and a metal end cap 234.

Figure 52:
FIG. 52 depicts a side view of a thin curved blade a sharp pointed end, a straight handle and a metal end cap.

FIG. 52 depicts a side view of a thin compound curved prosthesis blade 288 with a straight handle 274 and a metal end cap 234.

Figure 53:
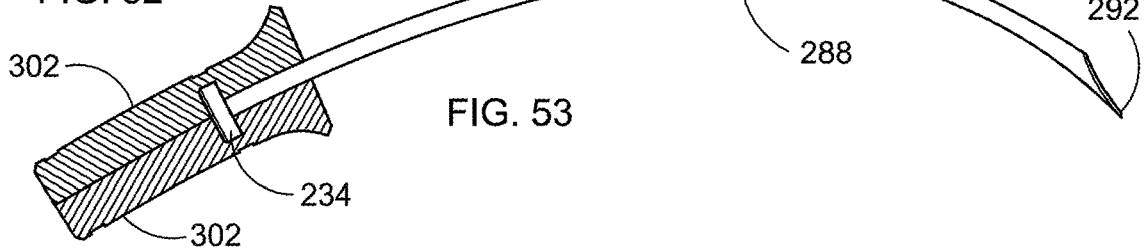
FIG. 53 depicts side view of a thin curved blade a sharp pointed end, a two part handle with the metal end cap enclosed.

FIG. 53 depicts side view of a thin compound curved prosthesis blade 288 with a two part handle 302 and the metal end cap 234 enclosed.

FIG. 54 depicts a perspective view of a large prosthesis 270, the compound curved prosthesis blade 288 with a two part blade guide ball 304 and a two part handle 302.

FIG. 55 depicts side view of a large prosthesis 270 the compound curved prosthesis blade 288 with a two part blade guide ball 304 and a two part handle 302 with the metal end cap 234 enclosed.

FIG. 56 depicts a perspective view of the female guide ball section 256 of the two part blade guide ball 304 where the female guide ball section 256 includes two wings on both sides of the female guide ball section 256.

FIG. 57 depicts a perspective view of the male guide ball section 260 of the two part blade guide ball 304 where the male guide ball section 260 includes two slots for accepting the wings located on both sides of the female guide ball section 256 (see FIG. 56).

FIG. 58 depicts a perspective view of the two part blade guide ball 304 assembled together, where the female guide ball section 256 two wings located on both sides of the female guide ball section 256 have mated with the two slots located on the male guide ball section 260 for accepting the wings located on both sides of the female guide ball section 256.

Figure 59:
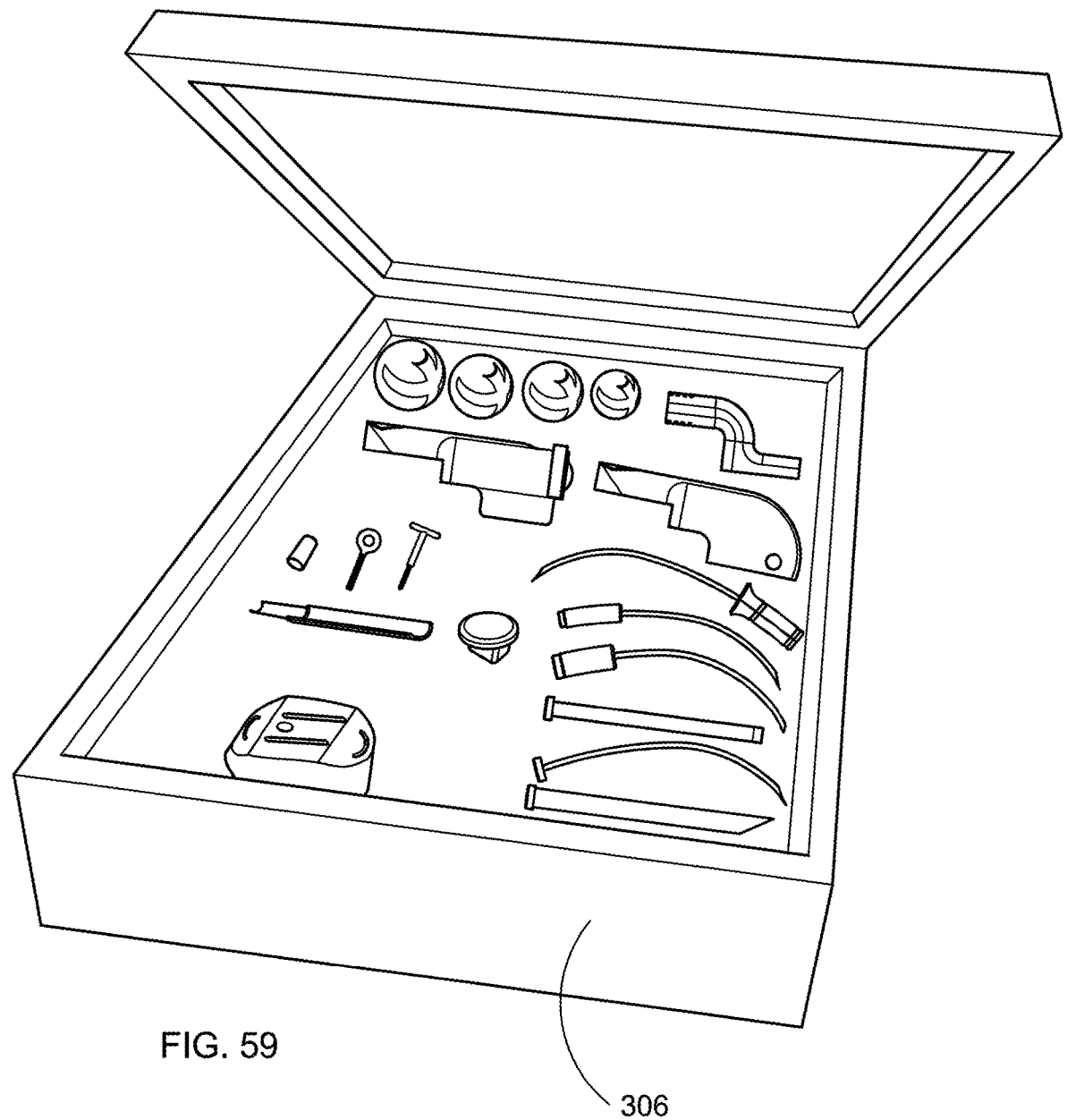
FIG. 59 depicts a perspective view of a box style of container illustrating a typical assortment of the prosthesis replacement equipment.

FIG. 59 depicts a perspective view of a box style of container 306 illustrating a typical assortment of prosthesis removal devices. It is anticipated that these assembled kits for performing joint revision surgery will contain any number, style and varying sizes of blade guide blocks, blade guide balls, curved knife blades, straight knife blades, narrow knife blades, wide knife blades, knife blades with attached knife blade handles, one-piece removable replacement knife blade handles, two-piece removeable replacement knife blade handles, eyebolts, T handle screws, T screws and possibly even a pneumatic osteotome.

The Joint Revision Surgery Apparatus 10A, 10B, 10C, 10D, 10E, 10F, 10G, 10H, 10J shown in the drawings and described in detail herein disclose arrangements of elements of particular construction and configuration for illustrating preferred embodiments of structure and method of operation of the present design. It is to be understood, however, that elements of different construction and configuration and other arrangements thereof, other than those illustrated and described may be employed for providing a Joint Revision Surgery Apparatus 10A, 10B, 10C, 10D, 10E, 10F, 10G, 10H, 10J in accordance with the spirit of this application, and such changes, alternations and modifications as would occur to those skilled in the art are considered to be within the scope of this application as broadly defined in the appended claims.

While certain embodiments, of the inventions have been described, these embodiments have been presented by way of example only, and are not intended to limit the scope of the disclosure. Indeed, the novel methods and systems described herein may be embodied in a variety of other forms. Furthermore, various omissions, substitutions and changes in the systems and methods described herein may be made without departing from the spirit of the disclosure. For example, one portion of one of the embodiments described herein can be substituted for another portion in another embodiment described herein. The accompanying claims and their equivalents are intended to cover such forms or modifications as would fall within the scope and spirit of the disclosure. Accordingly, the scope of the present inventions is defined only by reference to the appended claims.

Features, materials, characteristics, or groups described in conjunction with a particular aspect, embodiment, or example are to be understood to be applicable to any other aspect, embodiment or example described in this section or elsewhere in this specification unless incompatible therewith. All of the features disclosed, in this specification (including any accompanying claims, abstract and drawings), and/or all of the steps of any method or process so disclosed, may be combined in any combination, except combinations where at least some of such features and/or steps are mutually exclusive. The protection is not restricted to the details of any foregoing embodiments. The protection extends to any novel one, or any novel combination, of the features disclosed in this specification (including any accompanying claims, abstract and drawings), or to any novel one, or any novel combination, of the steps of any method or process so disclosed.

Furthermore, certain features that are described in this disclosure in the context of separate implementations can also be implemented in combination in a single implementation. Conversely, various features that are described in the context of a single implementation can also be implemented in multiple implementations separately or in any suitable subcombination. Moreover, although features may be described above as acting in certain combinations, one or more features from a claimed combination can, in some cases, be excised from the combination, and the combination may be claimed as a subcombination or variation of a subcombination.

Moreover, while operations may be depicted in the drawings or described in the specification in a particular order, such operations need not be performed in the particular order shown or in sequential order, or that all operations be performed, to achieve desirable results. Other operations that are not depicted or described can be incorporated in the example methods and processes. For example, one or more additional operations can be performed before, after, simultaneously, or between any of the described operations. Further, the operations may be rearranged or reordered in other implementations. Those skilled in the art will appreciate that in some embodiments, the actual steps taken in the processes illustrated and/or disclosed may differ from those shown in the figures. Depending on the embodiment, certain of the steps described above may be removed, others may be added. Furthermore, the features and attributes of the specific embodiments disclosed above may be combined in different ways to form additional embodiments, all of which fall within the scope of the present disclosure. Also, the separation of various system components in the implementations described above should not be understood as requiring such separation in all implementations, and it should be understood that the described components and systems can generally be integrated together in a single product or packaged into multiple products.

For purposes of this disclosure, certain aspects, advantages, and novel features are described herein. Not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments or that one or more embodiments necessarily include logic for deciding, with or without user input or prompting, whether these features, elements, and/or steps are included or are to be performed in any particular embodiment.

Conjunctive language such as the phrase "at least one of X, Y, and Z," unless specifically stated otherwise, is otherwise understood with the context as used in general to convey that an item, term, etc. may be either X, Y, or Z. Thus, such conjunctive language is not generally intended to imply that certain embodiments require the presence of at least one of X, at least one of Y, and at least one of Z.

Language of degree used herein, such as the terms "approximately," "about," "generally," and "substantially" as used herein represent a value, amount, or characteristic close to the stated value, amount, or characteristic that still performs a desired function or achieves a desired result. For example, the terms "approximately", "about", "generally," and "substantially" may refer to an amount that is within less than 10% of, within less than 5% of, within less than 1% of, within less than 0.1% of, and within less than 0.01% of the stated amount. As another example, in certain embodiments, the terms "generally parallel" and "substantially parallel" refer to a value, amount, or characteristic that departs from exactly parallel by less than or equal to 15 degrees, 10 degrees, 5 degrees, 3 degrees, 1 degree, or 0.1 degree.

The scope of the present disclosure is not intended to be limited by the specific disclosures of preferred embodiments in this section or elsewhere in this specification, and may be defined by claims as presented in this section or elsewhere in this specification or as presented in the future. The language of the claims is to be interpreted broadly based on the language employed in the claims and not limited to the examples described in the present specification or during the prosecution of the application, which examples are to be construed as non-exclusive.

Further, the purpose of the foregoing abstract is to enable the U.S. Patent and Trademark Office, foreign patent offices worldwide and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

I claim:

1. A joint revision surgery apparatus comprising:
   (a) a blade guide block having a solid frame including one or more orifices therein wherein said one or more orifices further includes one or more female threaded orifices configured to accept male threaded screws, handles and bolts for securing said blade wide block to an existing prosthesis implant;
   (b) a plurality of blade guide slots extending through said blade guide block configured to accept the insertion of and to guide the motion of a plurality of knife blades; and
   (c) a centrally located cavity within said blade guide block configured to be placed over the trunnion end of an existing prosthesis implant;
   wherein said blade guide block is placed over the trunnion end of an existing prosthesis implant and secured within said centrally located cavity, followed by the insertion and downward motion of a plurality of knife blades into said knife blade slots extending through said blade guide block to free the existing prothesis implant to facilitate removal of the existing prothesis implant during joint revision surgery.

2. The joint revision surgery apparatus according to claim 1, wherein said blade guide block having a solid frame includes a one-piece solid frame, and further wherein said one-piece solid frame varies in size depending on the size of the existing prothesis implant to be removed during joint revision surgery.

3. The joint revision surgery apparatus according to claim 1, wherein said blade guide block having a solid frame includes a two-piece solid frame assembly and further wherein said two-piece solid frame assembly includes an adjustable knife blade accepting orifice configured to adjust to accept knife blades of varying thicknesses.

4. The joint revision surgery apparatus according to claim 1, wherein said plurality of blade guide slots extending through said blade guide block configured to accept the insertion of and to guide the motion of a plurality of knife blades includes a plurality of blade guide slots configured to accept straight knife blades.

5. The joint revision surgery apparatus according to claim 1, wherein said plurality of blade guide slots extending through said blade guide block configured to accept the insertion of and to guide the motion of a plurality of knife blades includes a plurality of blade guide slots configured to accept curved knife blades.

6. The joint revision surgery apparatus according to claim 1, wherein said plurality of blade guide slots extending through said blade guide block configured to accept the insertion of and to guide the motion of a plurality of knife blades includes a plurality of blade guide slots configured to accept compound curved knife blades.

7. The joint revision surgery apparatus according to claim 1, wherein said blade guide block having a solid frame including one or more female threaded orifices therein includes female threaded orifices configured to accept male threaded set screws for securing said blade guide block to an existing prosthesis implant when the trunnion end of an existing prothesis implant is placed within said centrally located cavity, and said male threaded set screw is tightened down.

8. The joint revision surgery apparatus according to claim 1, wherein said blade guide block having a solid frame including one or more female threaded orifices therein includes threaded orifices configured to accept male threaded T handle screws for securing said blade guide block to an existing prosthesis implant when the trunnion end of an existing prothesis implant is placed within said centrally located cavity, and said male threaded T handle screw is tightened down.

9. The joint revision surgery apparatus according to claim 1, wherein said blade guide block having a solid frame including one or more female threaded orifices therein includes threaded orifices configured to accept male threaded eye bolts for securing said blade guide block to an existing prosthesis implant when the trunnion end of an existing prothesis implant is placed within said centrally located cavity, and said male threaded eye bolt is tightened down.

10. The joint revision surgery apparatus according to claim 1, wherein said blade guide blocks are assembled into a kit to be sold together, including kits which will contain any number, style and varying sizes of blade guide blocks, blade guide balls, curved knife blades, straight knife blades, narrow knife blades, wide knife blades, knife blades with attached knife blade handles, one-piece removable replacement knife blade handles, two-piece removeable replacement knife blade handles, eyebolts, T handle screws, and set screws.

11. A method of making a joint revision surgery apparatus comprising the steps of:
    (a) providing a blade guide block having a solid frame including one or more orifices therein wherein said one or more orifices further includes one or more female threaded orifices configured to accept male threaded screws, handles and bolts for securing said blade guide block to an existing prosthesis implant;
    (b) providing a plurality of blade guide slots extending through said blade guide block configured to accept the insertion of and to guide the motion of a plurality of knife blades; and
    (c) providing a centrally located cavity within said blade guide block configured to be placed over the trunnion end of an existing prosthesis implant;
    (d) providing curved knife blades, straight knife blades, narrow knife blades, wide knife blades, knife blades with attached knife blade handles, one-piece removable replacement knife blade handles, two-piece removeable replacement knife blade handles; and
    (e) providing male threaded eyebolts, T handle screws, and set screws configured to be threaded into said female threaded orifices:
    wherein when in use said blade guide block is placed over the trunnion end of an existing prosthesis implant and secured within said centrally located cavity, followed by the insertion and downward motion of a plurality of knife blades into said knife blade slots extending through said blade guide block to free the existing prothesis implant to facilitate removal of the existing prothesis implant during joint revision surgery.

12. The method of making a joint revision surgery apparatus according to claim 11, wherein said blade guide block having a solid frame includes a one-piece solid frame, and further wherein said one-piece solid frame varies in size depending on the size of the existing prothesis implant to be removed during joint revision surgery.

13. The method of making a joint revision surgery apparatus according to claim 11, wherein said blade guide block having a solid frame includes a two-piece solid frame assembly and further wherein said two-piece solid frame assembly includes an adjustable knife blade accepting orifice configured to adjust to accept knife blades of varying thicknesses.

14. The method of making a joint revision surgery apparatus according to claim 11, wherein said plurality of blade guide slots extending through said blade guide block configured to accept the insertion of and to guide the motion of a plurality of knife blades includes a plurality of blade guide slots configured to accept straight knife blades.

15. The method of making a joint revision surgery apparatus according to claim 11, wherein said plurality of blade guide slots extending through said blade guide block configured to accept the insertion of and to guide the motion of a plurality of knife blades includes a plurality of blade guide slots configured to accept curved knife blades.

16. The method of making a joint revision surgery apparatus according to claim 11, wherein said plurality of blade guide slots extending through said blade guide block configured to accept the insertion of and to guide the motion of a plurality of knife blades includes a plurality of blade guide slots configured to accept compound curved knife blades.

17. The method of making a joint revision surgery apparatus according to claim 11, wherein said blade guide block having a solid frame including one or more orifices therein further includes female threaded orifices configured to accept male threaded set screws for securing said blade guide block to an existing prosthesis implant when the trunnion end of an existing prothesis implant is placed within said centrally located cavity, and said male threaded set screw is tightened down.

18. The method of making a joint revision surgery apparatus according to claim 11, wherein said blade guide block having a solid frame including one or more orifices therein further includes female threaded orifices configured to accept male threaded T handle screws for securing said blade guide block to an existing prosthesis implant when the trunnion end of an existing prosthesis implant is placed within said centrally located cavity, and said male threaded set screw is tightened down.

19. The method of making a joint revision surgery apparatus according to claim 11, wherein said blade guide block having a solid frame including one or more orifices therein further includes female threaded orifices configured to accept male threaded eye bolts for securing said blade guide block to an existing prosthesis implant when the trunnion end of an existing prothesis implant is placed within said centrally located cavity, and said male threaded set screw is tightened down.

20. The method of making a joint revision surgery apparatus according to claim 11, wherein said blade guide blocks are assembled into a kit to be sold together, including kits which will contain any number, style and varying sizes of blade guide blocks, blade guide balls, curved knife blades, straight knife blades, narrow knife blades, wide knife blades, knife blades with attached knife blade handles, one-piece removable replacement knife blade handles, two-piece removeable replacement knife blade handles, eyebolts, T handle screws, and set screws.

* * * * *